United States Patent
Aben et al.

(10) Patent No.: US 11,723,722 B2
(45) Date of Patent: Aug. 15, 2023

(54) METHODS AND SYSTEMS FOR GUIDANCE IN CARDIAC RESYNCHRONIZATION THERAPY

(71) Applicant: PIE Medical Imaging BV, Maastricht (NL)

(72) Inventors: Jean-Paul Aben, Limbricht (NL); Chris Bouwman, Oirsbeek (NL)

(73) Assignee: Pie Medical Imaging B.V., Maastricht (NL)

( * ) Notice: Subject to any disclaimer, the term of this patent is extended or adjusted under 35 U.S.C. 154(b) by 681 days.

(21) Appl. No.: 16/630,833

(22) PCT Filed: Jul. 12, 2018

(86) PCT No.: PCT/EP2018/069011
§ 371 (c)(1),
(2) Date: Jan. 13, 2020

(87) PCT Pub. No.: WO2019/012066
PCT Pub. Date: Jan. 17, 2019

(65) Prior Publication Data
US 2020/0138521 A1   May 7, 2020

Related U.S. Application Data

(60) Provisional application No. 62/532,096, filed on Jul. 13, 2017.

(51) Int. Cl.
*A61B 34/10* (2016.01)
*G06T 7/11* (2017.01)
(Continued)

(52) U.S. Cl.
CPC ............ *A61B 34/10* (2016.02); *A61B 5/0044* (2013.01); *A61B 5/055* (2013.01); *A61B 5/349* (2021.01);
(Continued)

(58) Field of Classification Search
CPC ....... A61B 34/10; A61B 5/0044; A61B 5/055; A61B 5/349; A61B 6/4417; A61B 6/481;
(Continued)

(56) References Cited

U.S. PATENT DOCUMENTS 6,252,402 B1   6/2001   Sanfilippo et al.
7,332,912 B2   2/2008   Pittaluga et al.
(Continued)

OTHER PUBLICATIONS

Sasaki et al. 2013 Circ. Arrhythm. Electrophysiol. 6:1139-1147 (Year: 2013).*
(Continued)

*Primary Examiner* — Keith M Raymond
*Assistant Examiner* — Patrick M Mehl
(74) *Attorney, Agent, or Firm* — Gordon & Jacobson, P.C.

(57) ABSTRACT

A method for providing guidance in Cardiac Resynchronization Therapy (CRT) comprising: a) providing image data sets of the heart of a patient; b) creating a three-dimensional (3D) anatomical model of the cardiac structures; c) calculating myocardium infarct scar distribution; d) calculating heart mechanical activation data; e) superimposing the scar distribution and the mechanical activation data on the 3D anatomical model to obtain a 3D roadmap model including anatomical geometry and mechanical activation data. A corresponding device and computer program are also disclosed.

20 Claims, 21 Drawing Sheets

(51) Int. Cl.

| | |
|---|---|
| *A61B 5/00* | (2006.01) |
| *A61B 5/055* | (2006.01) |
| *A61B 6/00* | (2006.01) |
| *G06T 7/00* | (2017.01) |
| *G06T 17/00* | (2006.01) |
| *A61B 5/349* | (2021.01) |
| *A61B 90/00* | (2016.01) |
| *A61N 1/362* | (2006.01) |

(52) U.S. Cl.
CPC ............ *A61B 6/4417* (2013.01); *A61B 6/481* (2013.01); *A61B 6/503* (2013.01); *G06T 7/0012* (2013.01); *G06T 7/11* (2017.01); *G06T 17/00* (2013.01); *A61B 2034/105* (2016.02); *A61B 2090/367* (2016.02); *A61B 2576/023* (2013.01); *A61N 1/362* (2013.01); *G06T 2207/10081* (2013.01); *G06T 2207/10088* (2013.01); *G06T 2207/30048* (2013.01)

(58) Field of Classification Search
CPC .............. A61B 6/503; A61B 2034/105; A61B 2090/367; A61B 2576/023; A61B 2034/104; A61B 5/7425; G06T 7/0012; G06T 7/11; G06T 17/00; G06T 2207/10081; G06T 2207/10088; G06T 2207/30048; G06T 2207/20084; G06T 2207/10104; G06T 2207/10108; G06T 2207/10116; G06T 2207/10132; G06T 2207/20081; G06T 2207/30101; A61N 1/362; G16H 30/40

See application file for complete search history.

(56) References Cited

U.S. PATENT DOCUMENTS

| | | | |
|---|---|---|---|
| 8,700,128 | B2 | 4/2014 | Assis et al. |
| 9,256,936 | B2 | 2/2016 | Jacobs et al. |
| 2013/0072790 | A1 | 3/2013 | Ludwig et al. |
| 2013/0182929 | A1 | 7/2013 | Oshinski et al. |
| 2015/0206302 | A1* | 7/2015 | Chen ................ A61B 6/487 382/131 |
| 2017/0071675 | A1* | 3/2017 | Dawoud ............ A61B 5/0035 |
| 2017/0221205 | A1* | 8/2017 | Mountney ............ G06T 19/00 |

OTHER PUBLICATIONS

"2012 EHRA/HRS expert consensus statement on cardiac resynchronization therapy in heart failure: implant and follow-up recommendations and management", Daubert et al., Heart Rhythm 2012, 1524-1576 9(9), 1524-1576.
"2013 ESC Guidelines on Cardiac Pacing and Cardiac Resynchronization Therapy", Bignole et al., Europace (2013) 15 1070-1118.
"Advantages and applications of the centerline method for characterizing regional ventricular function", Sheehan et al., Circulation Aug. 1986;74(2):293-305.
"A meshfree radial point interpolation method (RPIM) for three-dimensional solids", Liu et al., Comput. Mech. 2005, vol. 36, No. 6, pp. 421-430.
An Integrated Platform for Image-Guided Cardiac Resynchronization Therapy, Ma et al., Phys. Med. Biol. 57 (2012) 2953-2968.
"A Registration-Based Propagation Framework for Automatic Whole Heart Segmentation of Cardiac MRI", Zhuang et al., IEEE Transaction on Medical Imaging Sep. 2010;29(9):1612-25.
"Automated myocardium segmentation in late gadolinium enhanced MR images", Qian et al., J Cardiovasc Magn Reson. 2014; 16 (Suppl 1): P346.
"Automatic coronary artery calcium scoring in cardiac ct angiography using paired convolutional neural networks", Wolterink et al., Medical Image Analysis 2016, p. 123-136.
"Automatic quantitative left ventricular analysis of cine MR images by using three-dimensional information for contour detection", Van Geuns et al., Radiology Jul. 2006;240(1):215-21.
"Cardiac MR perfusion image processing techniques: a survey", Gupta et al., Med Image Anal. May 2012;16(4):767-85.
"Deep learning", Lecun et al., Nature 521 (7553) (2015), p. 436-444.
"Different algorithms for quantitative analysis of myocardial infarction with DE MRI: comparison with autopsy specimen measurements", Gruszczynska et al., Acad Radiol. Dec. 2011;18(12):1529-36.
"Echocardiography for cardiac resynchronization therapy: recommendations for performance and reporting—a report from the American Society of Echocardiography Dyssynchrony Writing Group endorsed by the Heart Rhythm Society", Gorscan et al., J Am Soc Echocardiogr 2008, 21(3), 191-213.
"Image Segmentation Using Deformable Models", Xu et al., SPIE Press, Chapter 3, 129-174.
"Left ventricular lead placement in the latest activated region guided by coronary venous electroanatomic mapping", Rad et al., Europace 2015, 17(1):84-93.
"Linear algebra and its applications", Lay, 2012, 4th edition, p. 142-143.
"MRI Reconstructions of Human Phrenic Nerve Anatomy and Computational Modeling of Cryoballoon Ablative Therapy", Goff R. et al., Ann Biomed Eng. 2016; 44: 1097-1106.
"MRI to X-Ray Fluoroscopy Overlay for Guidance of Cardiac Resynchronization Therapy Procedures", Ma et al., Computing in Cardiology 2010;37:229-232.
"Non-rigid image registration: theory and practice", Crum et al., The British Journal of Radiology; 77 (2004), S140-S153.
"Patient assessment for cardiac resynchronization therapy: Past, present and future of imaging techniques" Auger et al., Canadian Journal of Cardiology 2010:26(1).
"Patient motion correction for multiplanar, multi-breath-hold cardiac cine MR imaging", Slomka et al., J. Magn. Reson. Imaging, vol. 25, No. 5, pp. 965-973, 2007.
"Relationship between mechanical dyssynchrony and intra-operative electrical delay times in patients undergoing cardiac resynchronization therapy". Suever, et al., J Cardiovasc Magn Reson vol. 16, 2014.
"Relative merits of left ventricular dyssynchrony, left ventricular lead position, and myocardial scar to predict long-term survival of ischemic heart failure patients undergoing cardiac resynchronization therapy", Delgado et al., Circulation 2011, 123(1):70-78.
"Right Ventricular Strain, Torsion, and Dyssynchrony in Realty Subjects using 3D Spiral Cine Dense Magnetic Resonance Imaging", Suever, et al., IEEE Transactions vol. 36, issue 5, 2017: pp. 1076-1085.
"Scattered data interpolation methods for electronic imaging systems: a survey" Amidror et al., J. Electron. Imaging 2002, vol. 11, No. 2: 157.
"Selecting Patients for Cardiac Resynchronization Therapy: Electrical or Mechanical Dyssynchrony?", Hawkins et al., European Heart Journal (2006) 27, 1270-1281.
Search Report and Written Opinon dated Oct. 11, 2018 of International Application No. PCT/EP2018/069011.
"Standardized Myocardial Segmentation and Nomenclature for Tomographic Imaging of the heart", Cerqueira et al., Circulation, vol. 105, 2002: pp. 539-542.
"Strategies to improve cardiac resynchronization therapy", Vernoov et al., Nat Rev Cardiol 2014, 11(8): 481-493.
"Targeted Left Ventricular Lead Placement to Guide Cardiac Resynchronization Therapy: The TARGET Study: A Randomized, Controlled Trial", Khan et al., Journal of the American College of Cardiology 2012, 59(17): 1509-1518.
"Three-dimensional quantification of regional left-ventricular dyssynchrony by magnetic resonance imaging" Mischi, et al., in Conf Proc IEEE Eng Med Biol Soc 2011: pp. 2646-2649.

* cited by examiner

1501

METHODS AND SYSTEMS FOR GUIDANCE IN CARDIAC RESYNCHRONIZATION THERAPY

CROSS REFERENCE TO RELATED APPLICATION(S)

This application is the national stage of International Patent Application No. PCT/EP2018/069011, filed Jul. 12, 2018, which claims priority to U.S. Provisional Patent Application No. 62/532,096, filed Jul. 13, 2017, the entire contents of which are herein incorporated by reference in their entireties.

FIELD OF THE INVENTION

The present disclosure relates to the technical field of medical imaging, particularly to the field of electrophysiology, although it can find application in any field where there is the need to pre-procedural and or procedural guidance.

STATE OF THE ART

Heart failure is a common disease in the Western world and rising up to 10% among people of 70 years and older. Heart failure is defined as a clinical syndrome characterized by clinical symptoms of breathlessness, ankle swelling, and fatigue. Approximately 25%-30% of patients diagnosed with heart failure demonstrate electrical conduction abnormalities of the hearth. Cardiac electrophysiology is a sub-discipline of cardiology enclosing the diagnosis and treatment of abnormal heart rhythms, also known as cardiac arrhythmia, cardiac dysrhythmia or irregular heartbeat. Cardiac arrhythmia is a group of conditions in which the heartbeat is irregular due to problems with the electrical conduction system of the heart. The term "arrhythmia" refers to any change from the normal sequence of electrical impulses, causing abnormal heart rhythms and can be caused by a variety of reasons, including age, heart damage, medications, and genetics.

In case cardiac arrhythmia reflects the two lower chambers of the heart, the contraction of the ventricles becomes uncoordinated. This condition is known as mechanical dyssynchrony and may be the result of blockage of a bundle branch block. During right bundle branch block (RBBB) for instance, the electrical conduction system travels from left to right, instead of simultaneously activating both ventricles. A blockage of the left branch bundle (LBBB) results consequently in a delayed activation of the left ventricle.

Cardiac resynchronization therapy (CRT) involves implanting a half-dollar sized device, usually just below the collarbone. Three wires (leads), one positioned in the right ventricle (RV), one in the right atrium and one in the left coronary vein (also identified as left ventricular lead) are connected to the device and monitor the contractions of the heart's ventricles to detect heart rate irregularities and emit tiny pulses of electricity to correct them. In effect, it is "resynchronizing" the heart and additionally stimulates the process of remodeling by reducing left ventricle (LV) volume.

CRT has been established as an effective treatment strategy for patients with heart failure showing significant reduction in mortality and morbidity, and improvements in quality of live. Despite the striking effectiveness of CRT in improving clinical outcomes as well as prognosis, a substantial proportion, up to 40% of patients who receive a CRT device, fails to benefit from this therapy, the so called 'non-responders'. Reasons for reduced benefit from CRT are attributed to: a) a suboptimal selection criteria for patients who receive CRT, and b) to suboptimal positioning of the left ventricular lead.

Suboptimal patient selection: According to the European heart rhythm association expert consensus paper, Daubert et al., "2012 *EHRA/HRS expert consensus statement on cardiac resynchronization therapy in heart failure: implant and follow-up recommendations and management*", Heart Rhythm 2012, 9(9), 1524-1576 as well as to Auger et al., "*Patient assessment for cardiac resynchronization therapy: Past, present and future of imaging techniques*", Canadian Journal of Cardiology 2010: 26(1), patients suitable for CRT are identified as; a) showing NYHA class III or IV heart failure symptoms, b) LV ejection fraction below 35% as normally assessed by echocardiography and c) evidence of dyssynchrony based on a prolongation of the QRS complex (>120 msec) as measured by electrocardiography (ECG).

Response to CRT is related to the presence of cardiac dyssynchrony prior to implantation as described by Gorcsan and coworkers in "*Echocardiography for cardiac resynchronization therapy: recommendations for performance and reporting—a report from the American Society of Echocardiography Dyssynchrony Writing Group endorsed by the Heart Rhythm Society*", J Am Soc Echocardiogr 2008, 21(3), 191-213. Delgado et al., "Relative merits of left ventricular dyssynchrony, left ventricular lead position, and myocardial scar to predict long-term survival of ischemic heart failure patients undergoing cardiac resynchronization therapy". Circulation 2011, 123(1):70-78, used a speckle tracking approach based on short-axis echocardiography to assess dyssynchrony by radial strain analysis. However, speckle tracking based on echocardiography can be technically challenging, particularly in regions of scar (myocardium infarct) in which signal amplitude is markedly reduced due to the physical limitations of ultrasound. Furthermore, ultrasound is very operator depending resulting in a high variability.

Suboptimal position of the LV lead: The implantation of a LV lead in patients is technically a rather complex procedure. Implantation training for CRT has a significant learning curve. Duration of implantation and fluoroscopic time can be substantial and implantation failure can be due to several reasons, such as inability to intubate the coronary sinus, unstable guiding delivery catheter, coronary vein stenosis or occlusion. The conventional approach as described in the European guidelines on cardiac pacing and CRT (Brignole et al., "2013 *ESC guidelines on cardiac pacing and cardiac resynchronization therapy: the task force on cardiac pacing and resynchronization therapy of the European Society of Cardiology (ESC). Developed in collaboration with the European Heart Rhythm Association (EHRA)*", Europace 2013, 15(8):1070-1118), defines a LV lead placement strategy based on anatomical information obtained during x-ray angiography (the imaging modality used during the implantation procedure), and target a coronary venous branch on the posterolateral wall. This strategy is based on the contention that the posterolateral wall is typically the latest activated site of the ventricle in patients with LV dyssynchrony caused by LBBB.

According to Vernooy and coworkers in "*Strategies to improve cardiac resynchronization therapy*", Nat Rev Cardiol 2014, 11(8): 481-493, optimal LV lead placement position is defined as the region with the latest electrical activation which is free from myocardium scar. The Targeted Left Ventricular Lead Placement to Guide CRT (TARGET) study by Khan et al., "*Targeted Left Ventricular Lead*

Placement to Guide Cardiac Resynchronization Therapy: The TARGET Study: A Randomized, Controlled Trial", Journal of the American College of Cardiology 2012, 59(17): 1509-1518, concluded that positioning the LV lead at the site of the latest mechanical activation and free of myocardium scar resulted in improved CRT response. Freedom of scar was defined as a radial strain amplitude>10%. However, echocardiographic strain analysis may not be the best technique to assess mechanical activation as well as regions of myocardium scar due to physical limitations of ultrasound and its high operator dependency.

Rad et al., "Left ventricular lead placement in the latest activated region guided by coronary venous electroanatomic mapping", Europace 2015, 17(1):84-93 demonstrated by a retrospective feasibility study that LV lead placement in the latest electrical activated region based on electro anatomic mapping (EAM) of the coronary veins is feasible and clinically practicable.

U.S. Pat. No. 8,700,128 describes a method to support the physician in lead placement by tracking the device over a 3-dimensional model of the coronary vein as obtained from a 3D coronary vein reconstruction based on two x-ray angiograms (venograms). The physician is able to activate the device at a random position and the system is able to superimpose the electrical response on the 3D model with the aim to support the physician to navigating the lead to an optimal location. However, this method does not take into consideration any location of myocardium infarct and furthermore, the guidance is based on result obtained by activating the device at a random location within the coronary vein, making the procedure still trial and error.

There is therefore a need for a more accurate, fully objective and reproducible approach to improve CRT.

SUMMARY OF THE INVENTION

It is thus an object of embodiments herein to provide image maps to be used as guidance in Cardiac Resynchronization Therapy and, more in general, for identifying regions to be considered optimal for receiving pacemaker leads.

In accordance with embodiments herein, devices, computer program products and computer implemented methods are provided for providing guidance in Cardiac Resynchronization Therapy (CRT), the devices, program products and methods comprising, under control of one or more computer systems configured with specific executable instructions,
  a) receiving image data sets of the heart of a patient;
  b) creating a three-dimensional (3D) anatomical model of the cardiac structures from at least one of the image data sets, comprising, for example, cardiac structures, infarct geometries, coronary vein geometry, phrenic nerve geometry or combination thereof;
  c) calculating myocardium infarct scar distribution from at least one of the image data sets;
  d) calculating heart mechanical activation data from at least one of the image data sets, for example, using myocardium 3D strain analysis, preferably by locating a time over a whole cardiac cycle corresponding to peak strain;
  e) superimposing the scar distribution and the mechanical activation data on the 3D anatomical model to obtain a 3D roadmap model including anatomical geometry and/or mechanical activation data and/or infarct scar distribution, for example by weighting the scar distribution with the mechanical activation data before superimposing to obtain a colour or grey value overlay on the endocardial or epicardial 3D geometry.

In an embodiment, the segment or zone of the heart, or an infarct free segment or zone of the heart, experiencing the latest mechanical activation is located and presented as outlined on the 3D anatomical model, such segment or zone being a candidate segment or zone for optimal pacemaker lead positioning in Cardiac Resynchronization Therapy.

In an embodiment, step c) comprises:
  segmenting myocardium infarct scar to provide a 3D surface mesh of the scar or receiving data comprising myocardium infarct scar segmentation; and
  computing myocardium scar distribution by weighting infarct transmurality, endocardial transmurality, epicardial transmurality and infarct homogeneity, wherein
  infarct transmurality is calculated as a percentage of the total infarct area inside the region covering the infarct;
  endocardial transmurality is calculated as the infarct transmurality weighted with a distance value from the endoardial boundary;
  the epicardial transmurality is the infarct transmurality weighted with a distance value from the epicardial border; and
  infarct homogeneity is calculated as the area of the detected infarct related to the area enclosed by a morphological close operator of the detected infarct.

The morphological close operator is typically configured to operate a division of the infarct area in chords and detect a non-infarct region between chords defining a patchy infarct region.

In an embodiment, the 3D roadmap model identifies regions located on coronary veins having the latest electrical activation which is free from myocardium scar as optimal left ventricle lead position or positions.

According to an embodiment, the heart mechanical activation calculation comprises:
  i) segmenting LV myocardium within a short-axis cine-MRI image sequence and a long-axis cine-MRI image sequence;
  ii) computing 3D strain by calculating 3D displacement field of the deformation of myocardium as segmented in i); and
  iii) generating a 3D model of the LV endocardium or LV epicardium of the heart based on the 3D strain computed in ii).

The mechanical activation of the heart is preferably color-coded on the surface of the 3D model by weighting mechanical activation with myocardium scar distribution.

According to an aspect, an electro anatomic mapping (EAM) model including 3D coronary vein anatomy and electrical activation timing is received and registered with the 3D roadmap model to determine optimal left ventricle lead position or positions.

In an embodiment, patient specific x-ray image data such as an x-ray venogram are received and registered with the 3D roadmap model to outline optimal left ventricle lead position or positions.

Embodiments herein relate also to a computer product directly loadable into the memory of a digital computer and comprising software code portions for performing the disclosed method claims when the product is run on a computer.

An embodiment provides for an apparatus for acquiring images data set of the heart of a patient, the apparatus comprising a data processing module configured to perform the method according to embodiments herein to determine a 3D roadmap for guidance in cardiac resynchronization therapy.

In an embodiment, the apparatus is an MRI apparatus is configured to acquire cine-MRI, delayed enhanced, coronary MRA or the like datasets.

According to an aspect, the MRI apparatus comprises in combination an x-ray apparatus configured to acquire x-ray venograms with or without contrast agents, the data processing module being configured to calculate a 3D roadmap model for assisting placement of pacemaker leads.

According to embodiments herein, a method of providing guidance to a user during a CRT implantation procedure, comprises:

i) generating a 3D model of different parts of the heart based on non-invasive three-dimensional anatomical imaging;

ii) generating a 3D model of mechanical activation of the heart based on non-invasive three-dimensional anatomical imaging;

iii) registering the 3D model of i) with the 3D model from ii) to produce a 3D roadmap model; and iv) using the produced 3D roadmap model of iii) to guide a user in placement of a pacemaker lead during the CRT implantation procedure.

The generating a 3D model of the different parts of the heart in i) advantageously includes generating a 3D model of a LV endocardium, epicardium, and myocardium scar.

In an embodiment, the method further comprises:
receiving an x-ray image data set comprised of multiple image frames over time; and
registering the 3D roadmap model produced in iii) with the x-ray image data set for use to guide the user in placement of the pacemaker lead during the CRT implantation procedure.

BRIEF DESCRIPTION OF THE DRAWINGS

The characteristics of the embodiments herein and the advantages derived therefrom will be more apparent from the following description of non-limiting embodiments, illustrated in the annexed drawings, in which.

DETAILED DESCRIPTION OF A PREFERRED EMBODIMENT

Figure 2A:
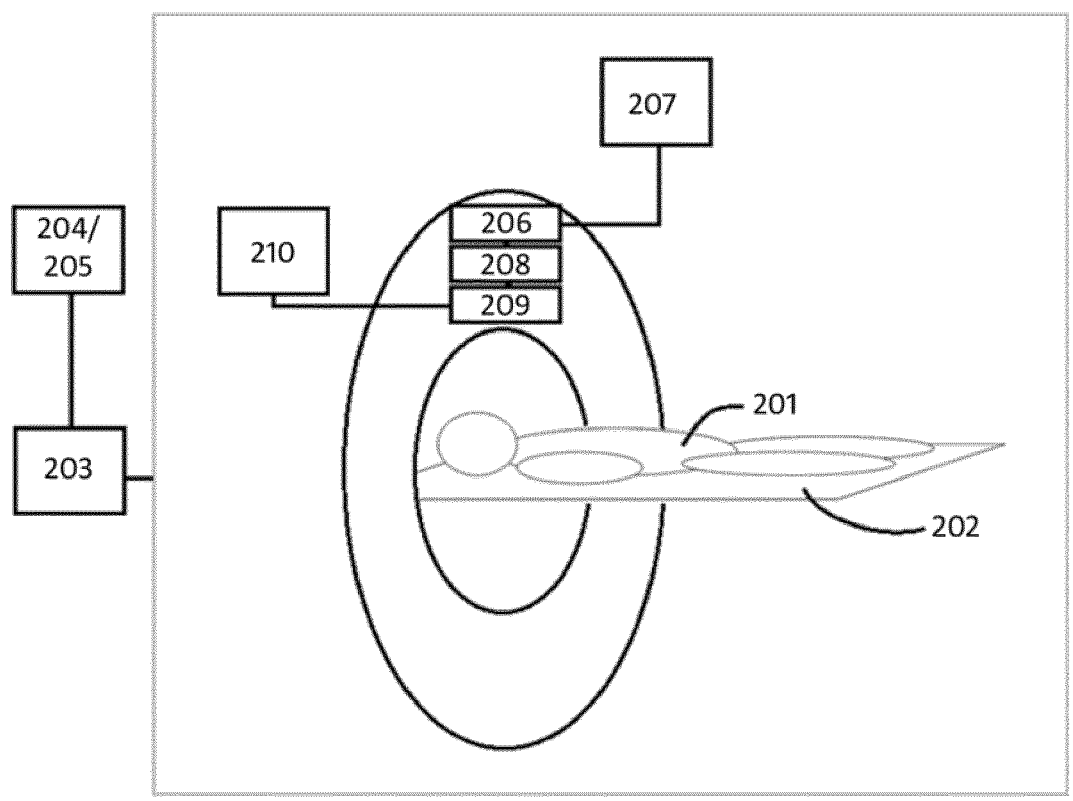
FIG. 2A shows an example of an MR unit block diagram in accordance with an embodiment herein.

A magnetic resonance imaging apparatus comprises an imaging unit configured to carry out sequential imaging. The apparatus applies a radiofrequency magnetic field onto a subject (i.e. patient) placed in a static magnetic field. A magnetic resonance signal generated from the subject is detected due to the application of the radio-frequency magnetic field. Using the detected signals an image is created. The magnetic resonance imaging apparatus also includes a gradient coil that adds spatial positional information to a magnetic resonance signal by applying a gradient magnetic field onto the subject. Using different combinations of radiofrequency pulses and gradients, different MRI sequences can be made. An MRI pulse sequence is a programmed set of changing magnetic gradients. Different pulse sequences allow the radiologist to image the same tissue in various ways, and combinations of sequences reveal important diagnostic information. FIG. 2A illustrates an example of a high-level block diagram of an MRI system. Portions of the system (as defined by various functional blocks) may be implemented with dedicated hardware, analogue and/or digital circuitry, and/or one or more processors operating program instructions stored in memory. The MRI system of FIG. 2A includes an adjustable table 202 for a patient 201, a data processing module 203 and a magnet system 206. The data processing module 203 includes one or more processors and memory that stores program instructions to direct the one or more processors to perform the operations described herein. The data processing module 203 also includes a display to present information to a user, such as the images, indicia, data and other information described herein and illustrated in the figures. The data processing module 203 also includes a user interface to receive inputs from the user in connection with operations herein, such as controlling operation of the imaging apparatus. For instance, scan parameters can be selected or altered, patient images may be displayed and post-processing can be performed, including, for example, region of interest measurements and visual and/or quantitative control selecting projection perspectives to be used when obtaining complementary images and the like. The data processing module 203 may correspond to or include portions of one or more of the systems described within the patents and publications referenced herein and incorporated by reference. One of the key aspects of an MRI system is the magnet system 206. The magnet system 206 generally comprises a large tube or a cylindrical magnet. The magnet is typically an electromagnet made from coils of superconducting wire typically helium cooled. The flow of electrical current through these coils produces a magnetic field. Permanent magnets can be used as well. The magnetic field has a certain field strength measured in Tesla. An important aspect of the magnet system 206 is the homogeneity of the magnetic field. That is a magnetic field, which changes very little over the specified region or volume. However, due to manufacturing imperfections or intervention room problems such as nearby steel posts, distortions of the magnetic field may arise. These inhomogeneities are corrected using a shim system 207. The corrections can either be performed manually or automatically. U.S. Pat. Nos. 6,252,402 and 7,332,912 disclose examples of shimming techniques for systems based on permanent magnets. In clinical MRI hydrogen, atoms of the human body are of importance. The nucleus of each hydrogen atom possesses spin also called nuclear spin angular momentum. That is, the nucleus of the hydrogen atom constantly rotates around an axis at a constant rate. When placed inside a magnetic field the nucleus the rotation axis tilts to align with the magnetic field. The strong static magnetic field produced by the magnet system 206 aligns the spins of each hydrogen atom of the human body in a certain frequency that is dependent on the strength of the magnetic field. Next, a radio frequency system 209 emits a radio frequency pulse (RFpulse) towards the part of the body being examined, tuned to a specific range of frequencies at which hydrogen protons move. This results that some of the hydrogen protons being moved 180 degrees out of alignment with the static magnetic field and being forced into phase with other hydrogen protons.

The radio frequency system 209 generally comprises transmitting coils.

The transmitting coil is usually built into the body of the scanner and transmits the RF-signal, generating an effective field perpendicular to the main magnetic field.

The energy, which is absorbed by different hydrogen atoms in the body, is then echoed or reflected back out of the body. The gradient system 208 is switched on and off to measure the echoes reflecting black out of the patient 201 and thus to localize the tissue signals. Generally, a gradient system 208 consists of one or multiple gradient coils and gradient amplifiers.

Gradient coils are usually loops of wire or thin conductive sheets on a cylindrical shell lying just inside the bore of an MRI scanner. When current is passed through these coils a secondary magnetic field is created. This gradient field slightly distorts the main magnetic field in a predictable pattern, causing the resonance frequency of protons to vary as a function of position. Typically, three sets of gradients are used: the x-, y- and z-gradients.

Each coil set is driven by an independent power amplifier and creates a gradient field whose z-component varies linearly along the x-, y- and z-direction respectively producing the orthogonal field distortion required for imaging.

A data acquisition system 210 then receives the echoes. The data acquisition system 210 is responsible for measuring the signals from the protons and digitizing them for later post-processing. In general, the data acquisition system 210 consists of a coil, a pre-amplifier and a signal processing system.

The coil detects the induced voltage form the protons following an RF pulse. The coil is tuned to the particular frequency of the returning signal. The pre-amplifier is a low-noise high gain amplifier located inside the magnet room or the coil itself in order to be able to process the signals produced by the protons.

Furthermore, the signal processing system provides for instance further amplification of the signal, demodulation into kHz signal, low-pass filer, divided into real and imaginary parts then detected by the analogue-to-digital converters (ADC). By applying an Inverse Fourier transformation (IFT) that converts the signal from the protons as mathematical data (k-space) into a picture that can be interpreted by the clinician.

The storage 204 is used to store the patient images that have been acquired immediately after they have been reconstructed. This is typically done in a universal language (vendor independent) such as DICOM (Digital Imaging and Communications in Medicine). The storage can be a hard disk or a PACS (picture archiving and communications system) server or a VNA (vendor neutral archive) 205.

Figure 2B:
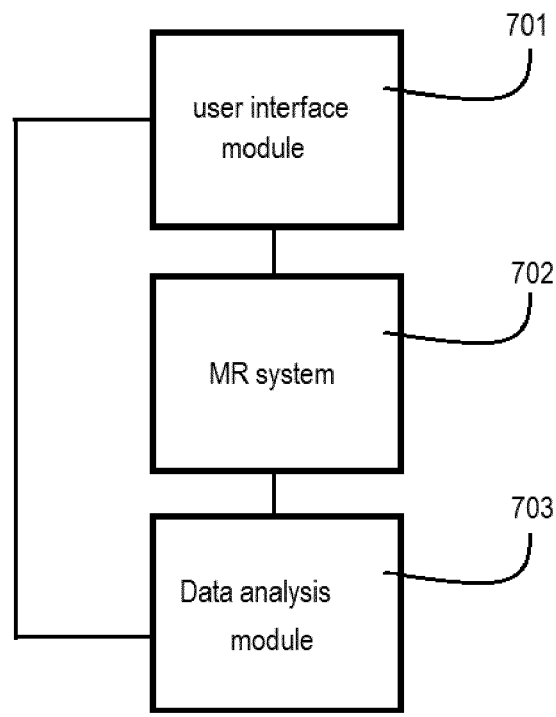
FIG. 2B shows a functional block diagram of an exemplary MRI acquisition of a MR system in accordance with an embodiment herein.

FIG. 2B is a functional block diagram of an exemplary MR acquisition in accordance to an embodiment herein which includes a MR system 702 that operates under commands from the user interface module and provide data to the data analysis module 703.

A clinician or other user acquires an MRI image of a patient 201 and stores this image on a hard disk 204 or a PACS or VNA server 205 in DICOM format. The MRI system 702 acquires MR data of a volume of interest for instance the heart and the aorta. The MR system typically includes a magnet system, a radio frequency system, a gradient system, a data acquisition system and a data storage.

The data analysis module 703 may be realized by a personal computer, workstation, or other computer processing system. The data analysis module 703 processes the acquired MR data of the MRI system 702 to generate, for instance, a 3D roadmap model. The user interface module 701 interacts with the user and communicates with the data analysis module 703. The user interface module 701 can include different kinds of input and output devices, such as a display screen for visual output, a touch screen for touch input, a mouse pointer or other pointing device for input, a microphone for speech input, a speaker for audio output, a keyboard and/or keypad for input, etc.

Figure 1:
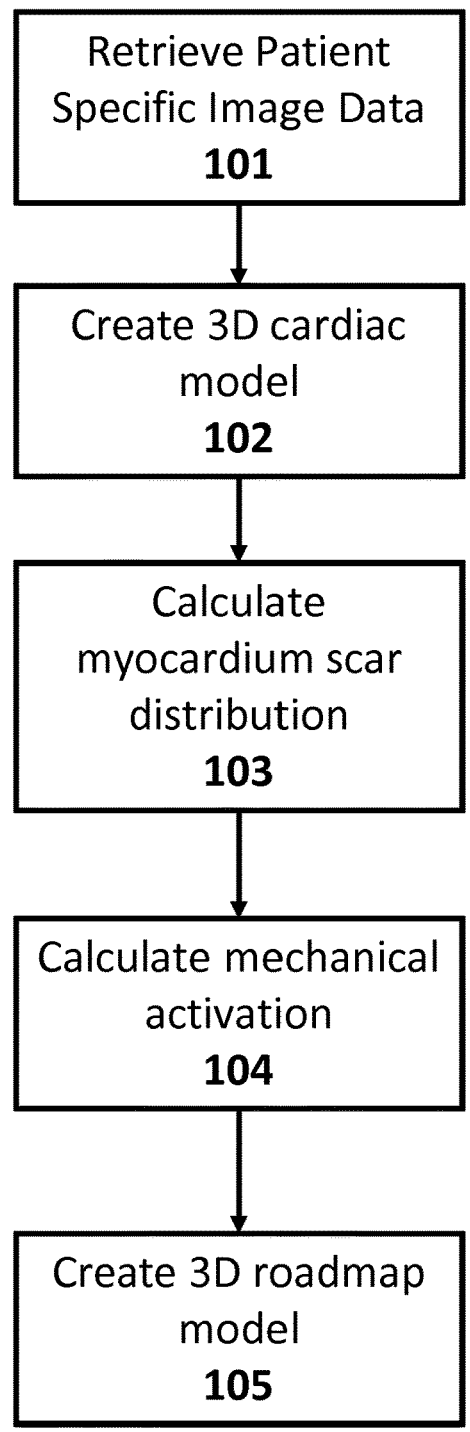
FIG. 1 shows a flowchart of the steps of the invention in a preferred embodiment.

An embodiment is now disclosed with reference to FIG. 1. The therein-depicted operations can, obviously, be performed in any logical sequence and can be omitted in parts. The objective of the embodiment as presented in FIG. 1 is to provide a roadmap which can be used by the physician (e.g. electrophysiologist) to prepare and or decide on optimal CRT treatment strategy.

As can be seen in FIG. 1, the workflow comprises of a number of steps. First patient specific image data is obtained as described in step 101 of FIG. 1. The patient specific image data is obtained during a non-invasive cardiac magnetic resonance imaging (MRI) examination. From this non-invasive MRI examination, standard cine-MRI both short-axis (SA) as well as long-axis (LA), and delayed enhanced MRI needs to be presents. Additionally, coronary MRA image data may be retrieved as well. Optionally, electro anatomic mapping (EAM) which includes both 3D coronary vein anatomy as well as the electrical activation timing may be retrieved in addition.

Figure 3:
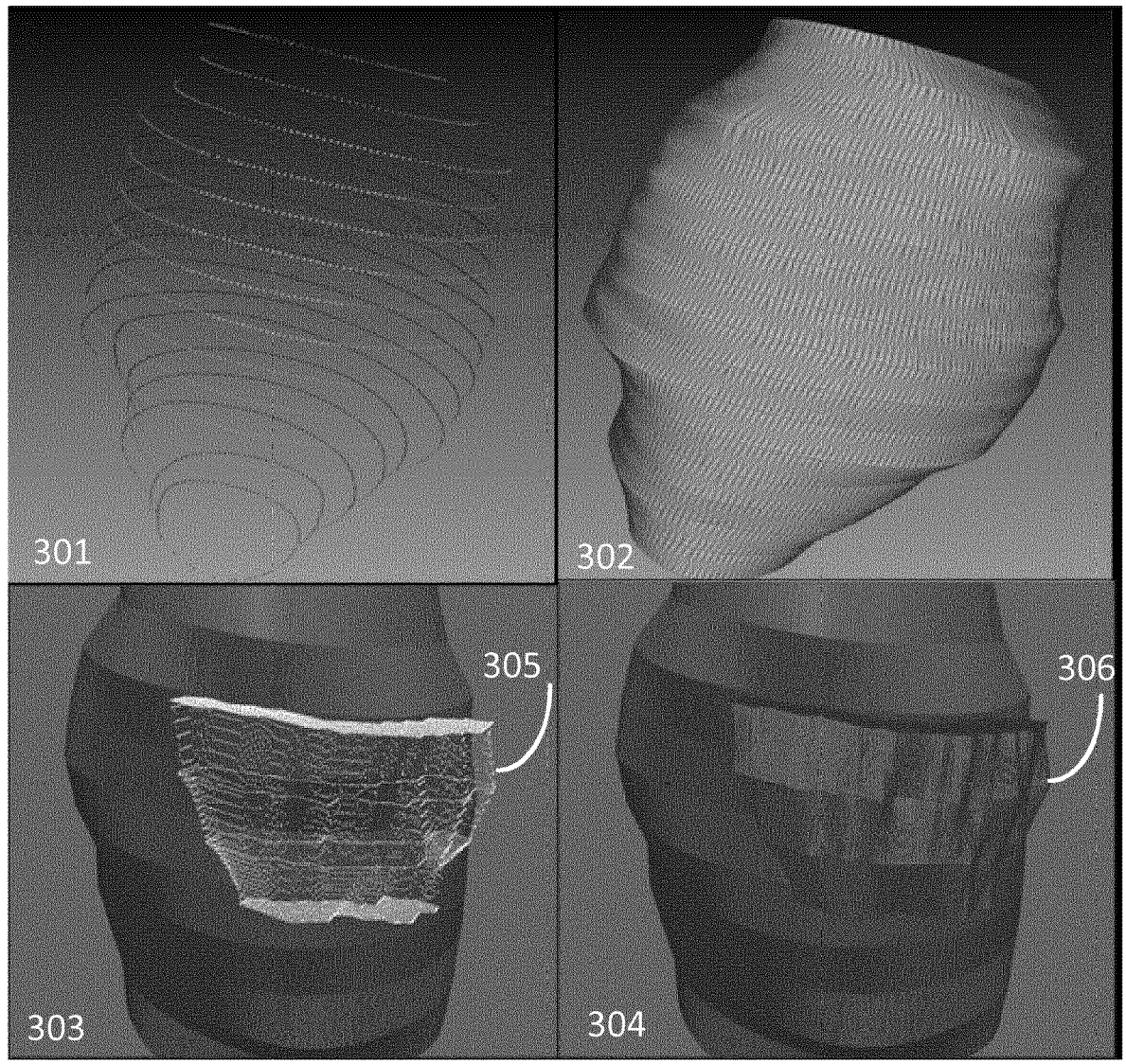
FIG. 3 visualize the methodology for creation of the 3D endocardial and 3D infarct model.
Figure 4A:
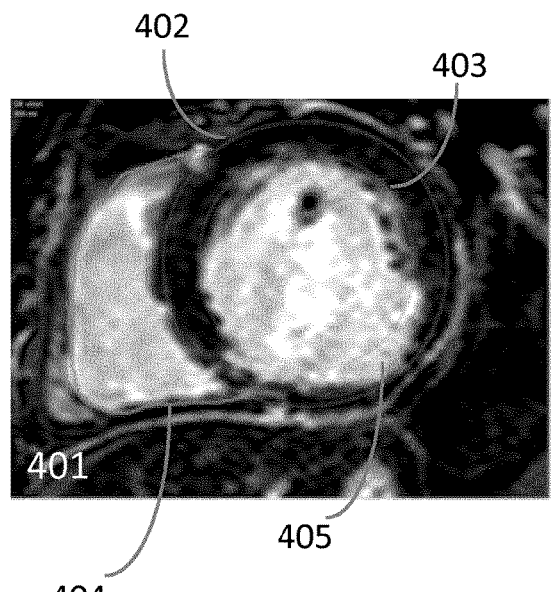
FIG. 4A shows an example of the 3D model which includes LV endocard, epicard, infarct and RV endocard.
Figure 4A:
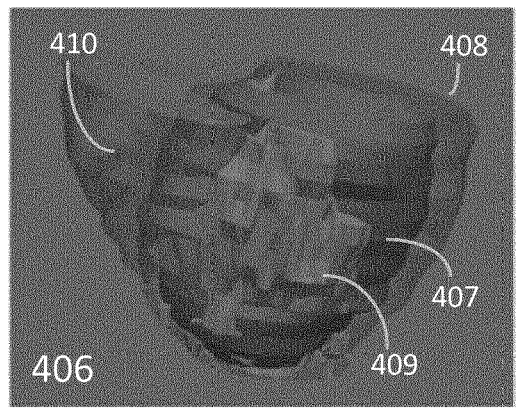

In step 102 of FIG. 1, the three-dimensional (3D) cardiac model is created. The methodology for creation of the 3D endocardial and 3D infarct model is visualized in FIG. 3. The cardiac 3D model is created at the cardiac phase in which the delayed enhanced patient specific image dataset is acquired. In general this represents the end-diastolic cardiac phase. A clinician or other user identifies (segments) the left ventricle (LV) myocardium boundaries (i.e. LV endocardial boundary and LV epicardial boundary, see for example FIG. 4A, label 403, 402) within the delayed enhanced patient specific image dataset. Optionally, the right ventricle (RV) blood pool (FIG. 4A, 404) is identified as well. Note that FIG. 4A, 401 shows one short-axis image-frame within the delayed enhanced patient specific image dataset. The segmentation can be performed manually by the user, semi-automatic or automatic. An example of semi-automatic is provided by van Geuns et al., "*Automatic quantitative left ventricular analysis of cine MR images by using three-dimensional information for contour detection*", Radiology 2006 July; 240(1):215-21. Within FIG. 3, label 301 shows in 3D the results of the endocardium segmentation encompassing the entire left ventricle from base to apex. In general, within a delayed enhanced patient specific image datasets, the LV enclosed approximately 25 slices (from base till apex). Where base refers to the location of the heart in which the LV blood pool is separated from the left atrium and ascending aorta by the mitral valve and aortic valve respectively and the apex represents the tip of the LV which is opposite to the base of the LV. The segmentation is normally performed in the two-dimensional (2D) image frames, and the translation towards 3D is accomplished by using the absolute system coordinates obtained from the MR imaging system through the DICOM headers. To obtain a 3D surface mesh, a triangulation between 3D coordinates of successive slices is performed to create a 3D surface mesh as shown by FIG. 3, 302. The same method can be used to generate a 3D surface mesh of the LV epicardium and RV endocardium (blood pool).

Segmentation of myocardium scar (FIG. 4A, 405) can be performed manually by the user, semi-automatic or automatic. An example of semi-automatic myocardium scar segmentation is provided by Gruszczynska et al., "*Different algorithms for quantitative analysis of myocardial infarction with DE MRI: comparison with autopsy specimen measurements*", Acad Radiol. 2011 December; 18(12):1529-36. Since myocardium scar is usually a complex 3D shaped, a different method is followed to generate the 3D surface mesh of the myocardium scar tissue. First, additional 3D coordinates are created based on interpolation between successive slices of the patient specific delayed enhanced image dataset of the 3D segmented scar boundaries (FIG. 3, 305). Next, a ray-trace based surface mesh algorithm is performed to create the final 3D scar surface mesh, as shown in FIG. 3, 306. An example of a 3D surface mesh of both the LV endocardium and 3D LV myocardium scar is shown in FIG. 3, 304. FIG. 4A, 406 shows a 3D surface mesh (3D cardiac model) in which the LV endocardium (407), LV epicardium (408), LV myocardium scar (409) and RV blood pool (410) are available. In the example provided by 406 within FIG. 4A, the RV myocardium scar is not present, although the same approach as described above can be used to generate a 3D surface mesh of the RV myocardium scar.

Figure 4B:
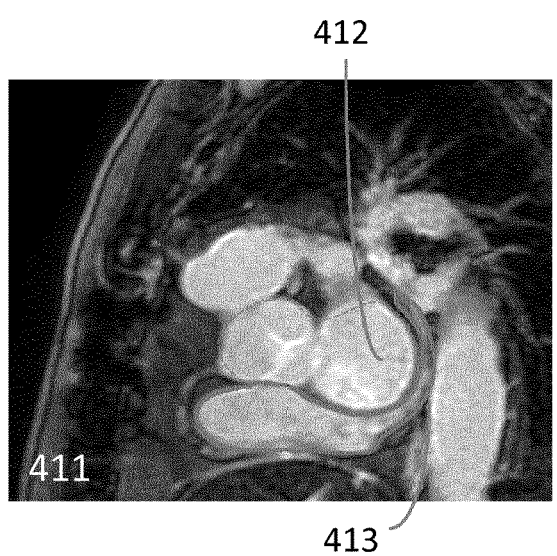
FIG. 4B shows an example the 3D model which includes LV endocard, epicard, infarct, RV endocard and coronary sinus based on short-axis MRI.
Figure 4B:
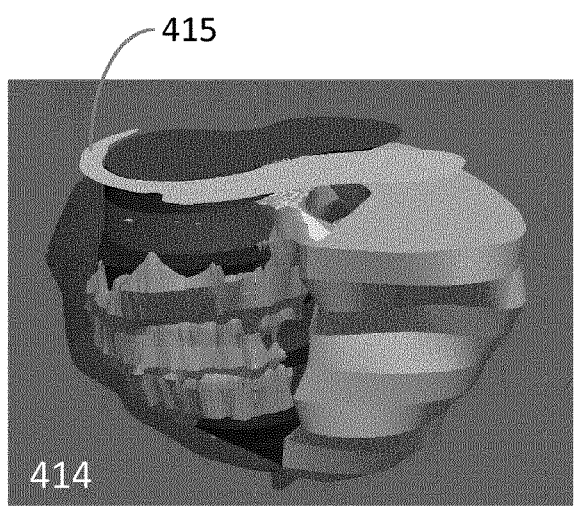

Optionally, the coronary sinus can be segmented (FIG. 4B, 413) within the patient specific delayed enhanced image dataset (FIG. 4B, 411). FIG. 4B, 414 shows the 3D cardiac model which includes the 3D representation of the coronary sinus (415).

Figure 5:
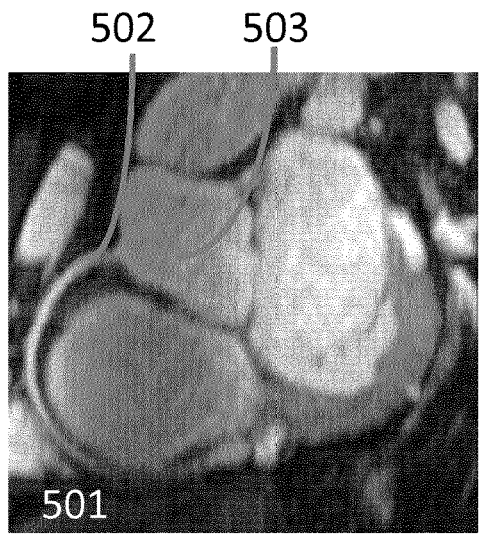
FIG. 5 shows an example of the 3D cardiac model with the 3D coronary vein geometry.
Figure 5:
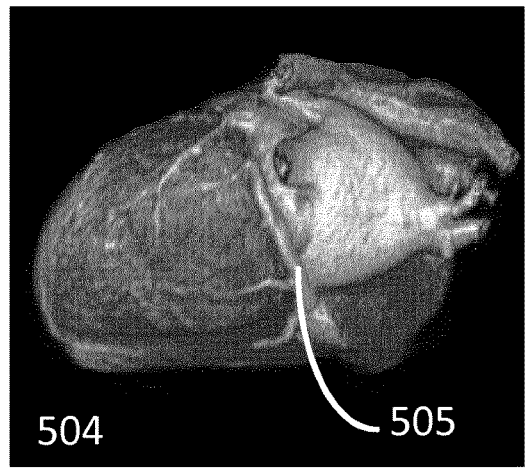
Figure 5:
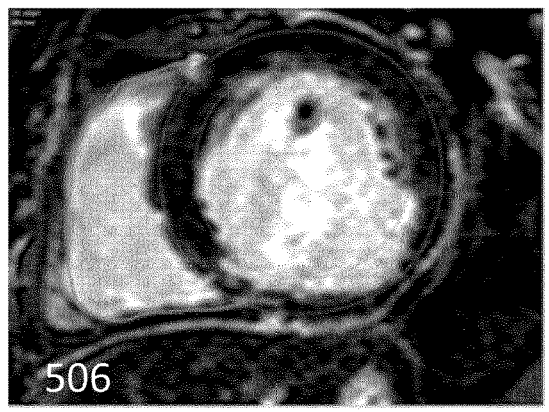
Figure 5:
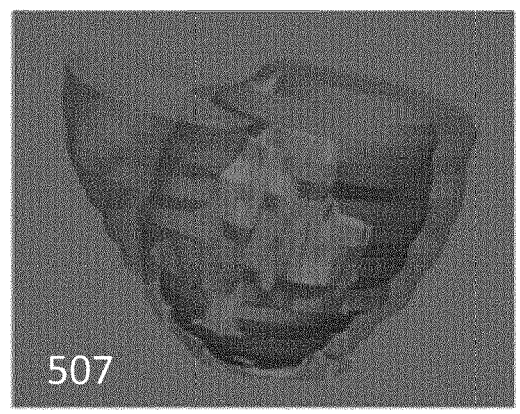
Figure 5:
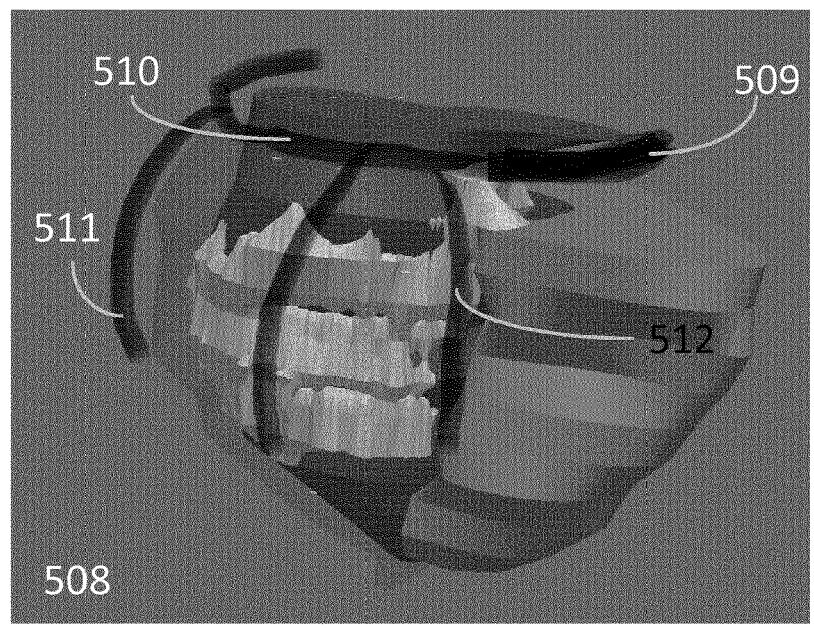

Optionally, a detailed 3D coronary vein geometry is added to the 3D cardiac model and reference is made to FIG. 5. This is achieved by extracting the 3D coronary vein geometry from a patient specific coronary magnetic resonance angiography (MRA) image dataset. FIG. 5, 501 shows an example of such a MRA dataset, in which the coronary sinus (502) is visible and emanating from the left atrium (503). FIG. 5, 504 shows a 3D volume rendered representation of the heart in which the coronary vein anatomy is visible (505). The detailed 3D coronary vein geometry is extracted by means of image segmentation techniques. For instance, the coronary veins can be segmented by means of a 3D deformable segmentation method (Xu et al, J. 2000. *Medical Image Segmentation Using Deformable Models. SPIE Press, Chapter* 3, 129-174).

Another method to segment to coronary veins is by use of machine learning algorithm. Machine learning is a subfield of computer science that "gives computers the ability to learn without being explicitly programmed". Evolved from the study of pattern recognition and computational learning theory in artificial intelligence, machine-learning explores the study and construction of algorithms that can learn from and make predictions on data—such algorithms overcome following strictly static program instructions by making data driven predictions or decisions, through building a model from sample inputs. Machine-learning is employed in a range of computing tasks where designing and programming explicit algorithms is infeasible. Machine-learning algorithms are widely used for processing of natural images (LeCun et al, "*Deep learning*", Nature 521 (7553) (2015), p 436-444) and since recently also in medical image analysis for classification and segmentation tasks, as for example provided by Wolterink et al, "*Automatic coronary artery calcium scoring in cardiac ct angiography using paired convolutional neural networks*", Medical Image Analysis 2016, p 123-136.

Given a dataset of images (e.g. coronary MRA) with known class labels (e.g. identification of the coronary vein anatomy, left ventricle, left atrium or the like), machine-learning system can predict the class labels of new images. There are at least two parts to any such system. The first part of the machine-learning is a feature extraction (extractor), being an algorithm for creating a feature vector given an image. A feature vector comprises a series of factors (e.g. multiple numbers) that are measured or extracted from the image dataset(s), which describe or characterize the nature of the object of interest, in our case the coronary vein anatomy. These features are then used by the second part of the system, a classifier, to classify unseen feature vectors extracted from the unseen image. Given a (large) database of images and extracted feature vectors whose labels are known and were used beforehand to train the machine-learning algorithm, classifying unseen images based on the features extracted the same way as in images with (known) labels (training images) is possible.

The features characterizing the coronary vein are extracted from the MRA dataset. For this, any engineered characteristic that describes the coronary vein characteristics (e.g. Gaussian, Haralick texture features) can be used. Also, coronary vein features as extracted by means of encoding methods such as convolution auto-encoder can be used. Any combination of these features can be selected. Convolutional autoencoder (CAE) is a technique for extracting features from image data. The aim of an auto-encoder is to learn a representation (encoding) for a set of data, typically for the purpose of dimensionality reduction. An auto-encoder is based on the encoder-decoder paradigm, where an input is first transformed into a typically lower-dimensional space (encoder part) and then expanded to reproduce the initial data (decoder part). It is trained in supervised or unsupervised fashion allowing it to extract generally useful features from unlabeled data, to detect and remove input redundancies and to present essential aspects of analyzing data in robust and discriminative representations. A CAE compress all the data from an image to a small vector from which it must contain enough information to reconstruct the image by the decoder. By this, the encoder is forced to learn features about the image being compressed.

Referring back to FIG. 5, the 3D cardiac model is expanded with the detailed coronary vein geometry. As explained above, the 3D coronary vein is extracted based on the patient specific MRA image dataset, and as described before and referring to FIG. 4A or 4B, the LV endocardium, LV epicardium, LV and/or RV myocardium scar and RV blood pool are extracted based on the patient specific delayed enhanced dataset (FIG. 5, 506 and 507).

Since the acquisition of the patient specific delayed enhance image dataset and the acquisition of the patient specific MRA image dataset is not acquired simultaneously, a registration has to be performed to align the two patient specific image datasets to a common coordinate system. In general a cardiac MR examination, acquires several image datasets. For instance, SA-cine MRI, LA cine-MRI, delayed enhance, coronary MRA, and the like are all acquired successively resulting that between these image datasets patient movement may be present. Alignment of the patient specific delayed enhanced image dataset with the patient specific MRA dataset can be performed by image registration techniques, as for instance described by Crum et al, "*Non-rigid image registration: theory and practice*", The British Journal of Radiology; 77 (2004), S140-S153, or by Zhuang et al, "*A Registration-Based Propagation Framework for Automatic Whole Heart Segmentation of Cardiac MRI*", IEEE Transaction on Medical Imaging 2010 September; 29(9):1612-25.

After this registration process, the segmented coronary vein geometry based on the patient specific MRA image dataset is combined with the 3D surface mesh of the cardiac structures based on the patient specific delayed enhanced image dataset as presented by 508 of FIG. 5. The coronary vein anatomy, resulting from the coronary vein segmentation, is visualized in a common coordinate system within the 3D cardiac model (508); coronary sinus (509), great cardiac vein (510), left marginal vein (511) and small cardiac vein (512).

During the CRT procedure, phrenic nerve stimulation should be avoided this to prevent chronic hiccups. Currently avoiding phrenic nerve stimulation is performed by additional actions during the implantation procedure. Optionally, the 3D geometry of the phrenic nerve is included in the 3D cardiac model (102). This can for instance be done by adding T2 weighted MRI to the patient specific image data (101) and extract the phrenic nerve as for instance taught by Goff R. et al., "*MRI Reconstructions of Human Phrenic Nerve Anatomy and Computational Modeling of Cryoballoon Ablative Therapy*", Ann Biomed Eng. 2016; 44: 1097-1106.

Figure 6:
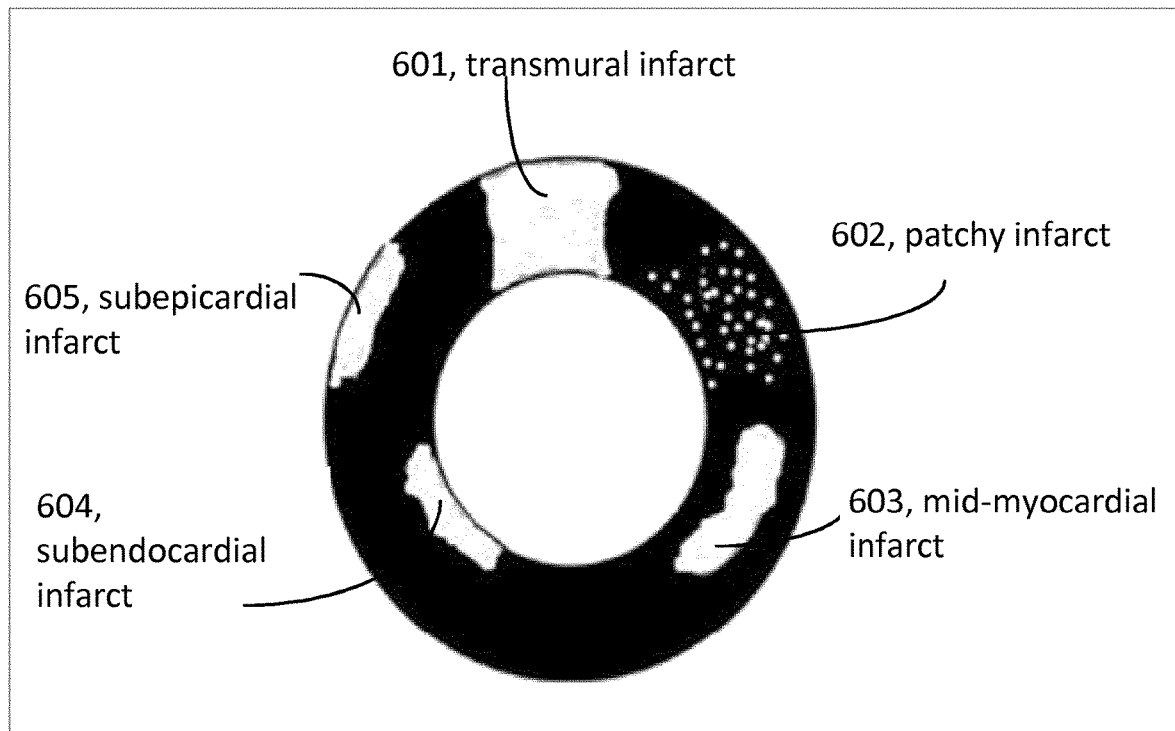
FIG. 6 shows an overview of the most common types of myocardium scar.

In step 103 of FIG. 1, the myocardium scar spatial distribution within the myocardium is calculated. Myocardium scar can be distributed differently across the myocardium. FIG. 6 shows an overview of the most common types of myocardium scar, in relation to scar homogeneity and scar spatial location within the myocardium. For instance, 601 shows a transmural infarct meaning an infarct that covers the full myocardium thickness. Such a region is not suitable for LV lead placement, since such a location will significantly hamper, or even block, the propagating of the induced electrical signal by the CRT device. The same holds for a sub-epicardial infarct (605), although propagation of the induced electrical signal by an electrode (LV Lead) placed at the endocardium of the LV (for instance the WiSE-CRT system from EBR Systems) may be effective. In case the infarct is sub-endocardial (604), LV lead placement by epicardial vein would again hamper the propagating of the induced electrical signal by the CRT device and a mid-myocardium infarct (603) potentially hampers the propagating of the induced electrical signal by both approaches; endocardium as well as epicardial. Furthermore, the propagating of the induced electrical signal will be unpredictable in case of patchy micro infarcts (602).

Figure 7:
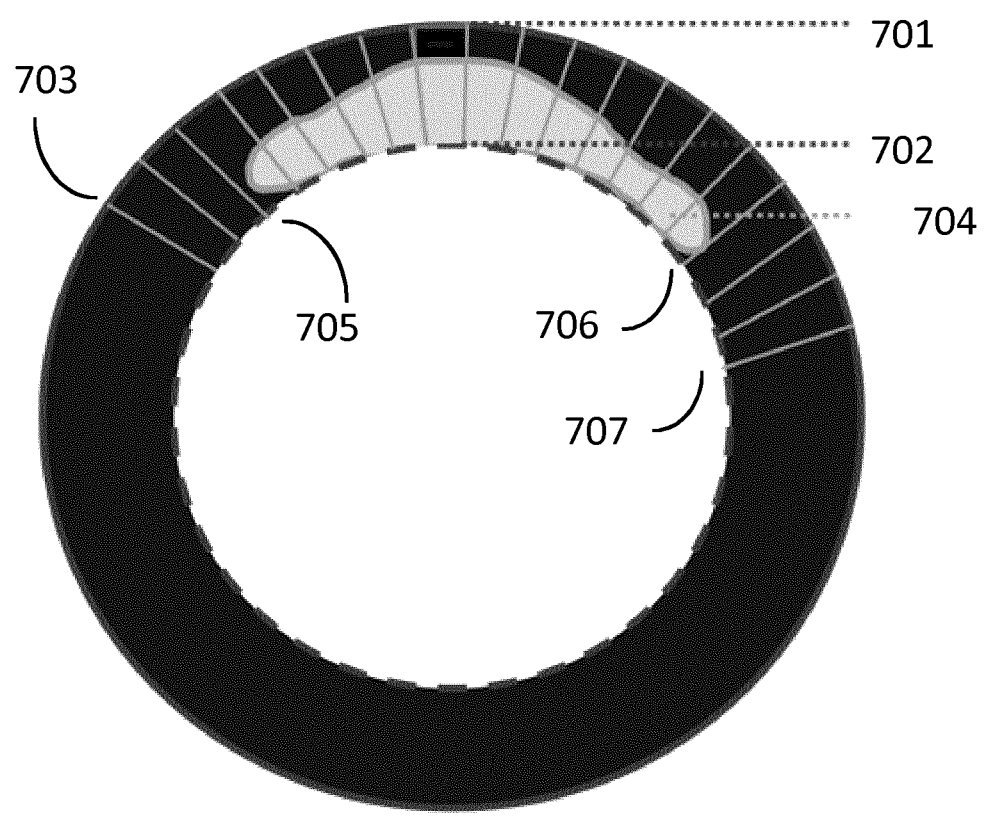
FIG. 7 shows an example of the calculation of myocardium scar distribution.

To quantify the scar homogeneity and scar spatial location within the myocardium reference is made to FIG. 7. The epicardial boundary (701) and endicardial boundary (702) needs to be segmented. This can be done either by manual or (semi)-automatic approach. An example of an automatic segmentation method is described by Qian et al., "*Automated myocardium segmentation in late gadolinium enhanced MR images*", J Cardiovasc Magn Reson. 2014; 16 (Suppl 1): P 346. The next step is to segment the infarct(s) within the myocardium as described previously. Next the myocardium wall is divided into several regions, for instance by using the Sheehan centerline algorithm as described by Sheehan et al., "*Advantages and applications of the centerline method for characterizing regional ventricular function*", Circulation 1986, August; 74(2):293-305. Other methods can be used as well, for instance a radial subdivision algorithm, in which the myocardium is divided into regions defined by the radial origination from the center of the ventricle towards the epicardial boundary. Within FIG. 7, the centerline algorithm is used to divide the myocardium into 100 regions by 99 chords (FIG. 7, 703). The infarct transmurality is calculated as the infarct area as a percentage of the total infarct area inside the region covering the infarct. In FIG. 7, this is identified by chord 705 and 706. The endocardial transmurality is calculated the same way as the infarct transmurality with the additional that each region is weighted with a distance value. In case the distance between the endocardial boundary (702) and infarct boundary (closest to endocardial boundary) is for instance within one pixel size, this weight is 1, otherwise 0. For the epicardial transmurality, the same approach is used, instead the distance is taken form epicardial boundary (702) to infarct boundary (closest to epicardial boundary). Different weight functions can be defined, for instance a nonlinear weight as function of the distance between infarct and the boundary of interest.

To assess infarct homogeneity, area of the detected infarct related to the area enclosed by the morphological close operator of the detected infract is calculated. Within image processing, a morphological close operator fills gabs within a predefined region. To identify this region, use is made of the chords (703), the region is defined as the first chord in which an infarct spot is identified up to the last chord. To allow correct detection of a patchy infarct region (FIG. 4,

402), an empty region (no infarct between chords) is allow. This empty region could be for instance one region. In the example of one allowed empty region, an allowed patchy infarct region size would than defined as a region between chords 706 and 707.

As previously mentioned, it is useful to calculate the final myocardium scar distribution depending on placing the electrode epicardial (inside a coronary vein) or placing the electrode endocardial. This placement choice will be known upfront to the CRT procedure, or this choice is a result of the output of step 105 to support the physician in planning the CRT procedure. The final myocardium scar is computed by the following equation (equation 0):

$$\text{final myocardium scar distribution} =$$
$$\alpha * \text{infarct transmurality} + \beta * \text{epicardial transmurality} +$$
$$\gamma * \text{endocardial transmurality} + \delta * (1 - \text{infarct homogeneity})$$

In which the parameters will be different between epicardial and endocardial placement of the electrode. For instance, the value of parameter $\beta$ will be less than the value for parameter $\gamma$ in case of an endocardial approach. The last step will be to normalize the final myocardium scar distribution.

Optionally, myocardium ischemia can be incorporated in the myocardium scar distribution. Myocardium ischemia refers to impedes oxygen delivery to the heart muscle and is primarily caused by coronary artery stenosis (narrowing, usually due to atherosclerosis). Placing the LV lead at a side (region) which suffers from myocardium ischemia would preferable be avoided, since the myocardium muscle can be considered as 'damages'. It would also provide additional information to the physician to evaluate if a percutaneous coronary intervention procedure (PCI), should be considered first, before performing or considering a CRT procedure. PCI is a minimal invasive procedure used to treat narrowing (stenosis) of the coronary arteries of the heart. Myocardium ischemia can be assessed by means of a MRI perfusion image dataset. Several methods can be used to calculate myocardium perfusion as described by Gupta et al., "*Cardiac MR perfusion image processing techniques: a survey*", Med Image Anal. 2012 May; 16(4):767-85. The calculated perfusion can be incorporated into equation 0 by adding for instance the weighted perfusion results to the equation. Optionally, the coronary arties can be segmented based on the MRA image datasets and the 3D geometry can be included in the 3D cardiac model.

In step 104 of FIG. 1, the latest mechanical activation of the myocardium is calculated. The heart's pumping action is regulated by its own electrical conduction system that coordinates the contraction of the various chambers of the heart. A normal heartbeat starts when an electrical impulse is fired from the sinus node (also called sino-atrial or SA node), in the right atrium. The sinus node is responsible for setting the rate and rhythm of the heart and is therefore referred to as the heart's pacemaker. The electrical impulse fired from the sinus node spreads throughout the atria, causing them to contract and squeeze blood into the ventricles. The electrical impulse travels from the sinus node to the atrioventricular node (also called AV node). There, impulses are slowed down for a very short period, and then continues down the conduction pathway via the bundle of His into the ventricles. The bundle of His divides into right and left pathways, called bundle branches. At the base of the heart, the bundles start to divide further into the purkinje fibers. When the impulses reach these fibers, they trigger the muscle fibers in the ventricles to contract. In the healthy heart, a synchronized electrical activation between left- and right-bundle leads to a synchronized mechanical contraction of the left and right ventricle and consequently a good pump function. In case this synchronization in electrical activation is distributed, the heart will contract in a desynchronized manner as for instance in case of LBBB. There is a strong correlation between electrical activation and the resulting mechanical activation, as has been reported by Suever, et al. in "*Relationship between mechanical dyssynchrony and intra-operative electrical delay times in patients undergoing cardiac resynchronization therapy*". J Cardiovasc Magn Reson vol 16, 2014. To assess the mechanical activation, a strain analysis of the myocardium is deployed.

Myocardium strain is a measure for regional or global deformation of the myocardium, in which the term deformation refers to the myocardium changes in shape and dimension during the cardiac cycle. For instance in case of bundle branch block, either LBBB or RBBB, there is a regional heterogeneity of deformation within different regions of the myocardium. Myocardial deformation, or strain analysis is commonly performed according to the local coordinate system aligned with the three cardiac axes: radial, circumferential and longitudinal. Within FIG. 8, these three orientations are presented, 801 the longitudinal strain, 802 the circumferential strain and 803 the radial strain. To assess all those three strain components, use is made of the standard MRI cardiac acquisition; a short-axis cine-MRI image dataset (808), and one or more long-axis cine MRI image dataset (805, 806, 807). Within the short-axis dataset (808), circumferential strain (802) and radial strain (803) can be assessed. Within the long-axis dataset, the longitudinal (801) and radial strain (803) can be assessed. These 2D strain components are computed by first defining the deformation by means of image registration techniques and then compute the strain based on the deformation. Strain is defined as the relative change in length. Within the Lagrangian formula of strain is, $\varepsilon L=(L-L0)/L0=\Delta L/L0$, where L0 is baseline length and L is the resulting length, defines strain in relation to the original length as a dimensionless measure, where shortening will be negative, and lengthening will be positive. It is usually expressed in percent. An alternative definition, Eulerian strain defines the strain in relation to the instantaneous length: $\varepsilon E=\Delta L/L$. For a change over time, the Lagrangian strain will be: $\varepsilon L=\Sigma \Delta L/L0$, and Eulerian Strain $\varepsilon E=\Sigma(\Delta L/L)$.

Figure 9:
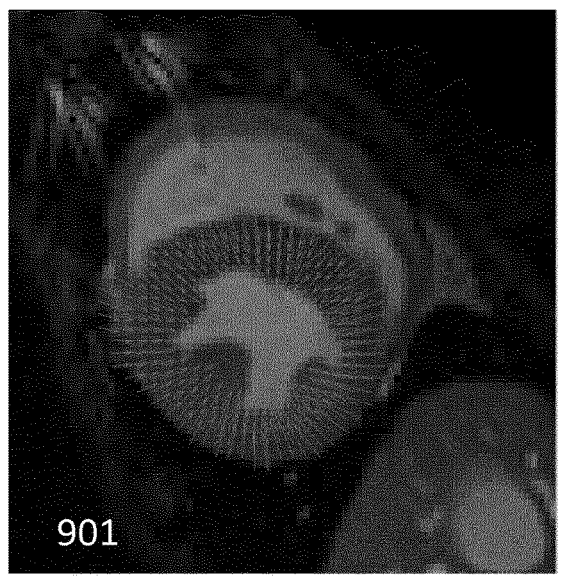
FIG. 9 shows an example of the calculated displacement field within a short-axis cine-MRI image dataset including an example of the circumferential strain.
Figure 9:
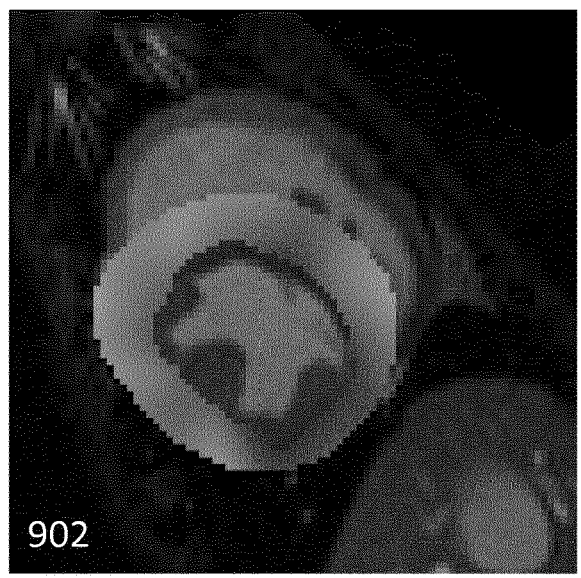

An example to define the deformation by means of image processing is by using a block matching algorithm. A block matching algorithm considered a block around each pixel (x,y) in a reference image $I_r$ within a region of interest. The reference image $I_r$ can for instance be the end-diastolic time point within the cardiac cycle and the region of interest the myocardium as identified by segmentation methods as for instance by Geuns et al., "*Automatic quantitative left ventricular analysis of cine MR images by using three-dimensional information for contour detection*", Radiology 2006 July; 240(1):215-21. The region of interest may be dilated to include surrounding myocardium tissue. The block around each pixel (x,y) can be defined as any shape and size. With the help of a similarity measure we are looking for a similar or equal block in the second image frame (next time moment within the cardiac cycle). This image differs from the first due to time and is called floating image $I_f$. This process can be described as $$\max_u S(P_{I_r}(x,y), P_{I_t}(x+u_x, y+u_y)) \quad \text{eq. 1}$$

with the similarity S and the patches P around the pixels. $u_x$ and $u_y$ characterize the displacement (deformation) in both x- and y-direction. The similarity should be maximized, so the most related patches are selected. As similarity measure S, the Cross Correlation may be used with the amount of pixels in one patch. Optionally, to efficiently calculate large displacements a pyramidal approach is used. Pyramidal approach divides the processing in several levels. For each level within the pyramid, the images are downscaled and a displacement field is calculated, starting from the highest level where the image is downscaled the most to the lowest level where the full resolution image is processed. The resulting displacement field from each level is used as a start for the next level within the pyramid. This process is repeated for all images within one cardiac cycle to obtain the 2D deformation along one cardiac cycle. FIG. 9 label 901 shows an example of the calculated displacement field within a short-axis cine MRI dataset. The example shows the displacement vector between two successive short-axis cine MRI image frames superimposed on one image.

As mentioned before the strain can be obtained from the Lagrangian deformation and can be mathematically derived from the deformation gradient $\nabla u$.

$$[E] = \frac{1}{2}((I - \nabla u)^T (I + \nabla u) - I) \quad \text{eq. 2}$$

$$E = \begin{bmatrix} E_{xx} & E_{xy} \\ E_{yx} & E_{yy} \end{bmatrix} \quad \text{eq. 3}$$

Where I describes the identity matrix and $[\nabla u]$ the displacement gradient and [E] the strain tensor. This definition of strain would be in x and y direction of the used image and does not correspond with the way the myocardium moves. Therefore another coordinate system is introduced in which the Cartesian strain or displacement is transformed into a local cylindrical coordinate system. Where the radial axis R (FIG. 8, 803) is perpendicular to the myocardium and pointing away from the cavity, the longitudinal axis Lo (FIG. 8, 801) is perpendicular to the R axis and pointing towards the base of the ventricle and the circumferential axis C (FIG. 8, 802) is perpendicular to R and L axis.

$$E_p = [R]^T [E][R] \quad \text{eq. 4}$$

With $E_p$ representing the (cylindrical/polar) strain tensor and R the rotation matrix. In the 2D cine MRI image dataset, the local coordinate system will depend on whether it is a short-axis or long-axis orientation. In the short-axis cine MRI dataset (FIG. 8, 808) radial and circumferential strain direction to the ventricle is defined by:

$$E_p = \begin{bmatrix} E_{rr} & E_{rc} \\ E_{cr} & E_{cc} \end{bmatrix} \quad \text{eq. 5}$$

FIG. 9, label 902 shows the circumferential strain component resulting from the displacement as shows in 901. In the long-axis cine MRI dataset (FIG. 8, 805-806-807) the local coordinate system is obtained by defining a line from the base to the apex of the left ventricle, and Ep will then represent radial and longitudinal components of left ventricle strain:

$$E_p = \begin{bmatrix} E_{rr} & E_{rl} \\ E_{lr} & E_{ll} \end{bmatrix} \quad \text{eq. 6}$$

The line is defined using two points, for instance by averaging the ends of the endocardial and epicardial contours and the second point by finding the most distant point belonging to the endocardial contour relative to the first point, which should correspond to the apex of the ventricle.

Figure 11:
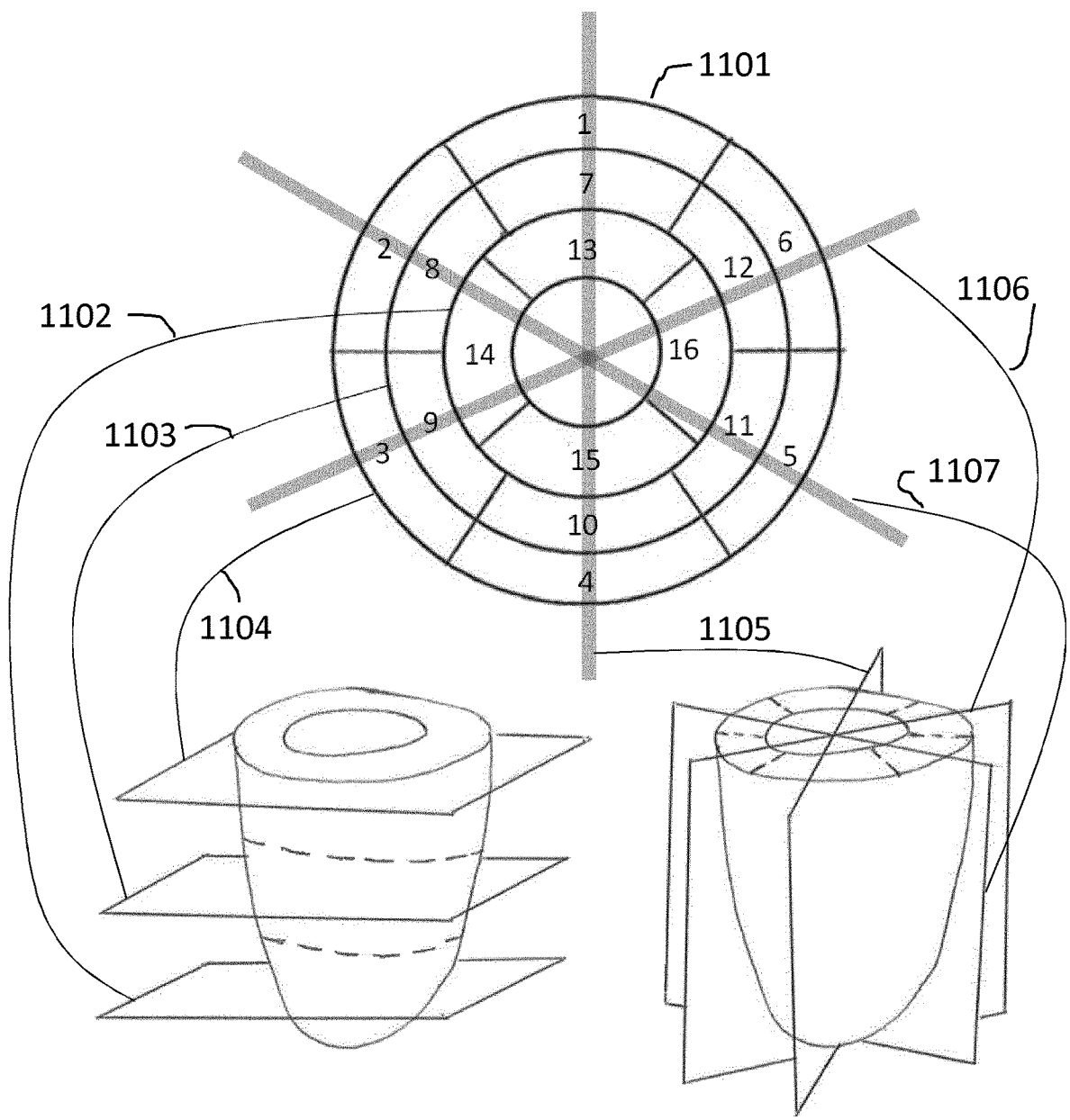
FIG. 11 shows the 16-segment model of the American Heart Association including a visual representation of combining the multiple LA and SA cine-MRI datasets into this 16-segment model.

Optionally, the 2D strains obtained from short-axis and long-axis cine MRI dataset can be put into a 3D model that represent the whole heart. One of such model is the 16 segments model of the American Heart Association (AHA), as shown as 1101 at FIG. 11. This model, which will be named as 16 AHA segment model for the rest of the document, is explained by Cerqueira, et al., in "*Standardized Myocardial Segmentation and Nomenclature for Tomographic Imaging of the heart*", Circulation, vol. 105, 2002: pp. 539-542. In brief, from the base to the apex, the heart is divided into 3 sections: basal, mid-cavity, and apical which each of the section is then divided into 6, 6, and 4 segments, respectively. The total number of segments yield 16 segments, hence the name 16 AHA segments. The 2D strains values, coming from the short-axis (in case of three short-axis cine-MRI datasets: 1102, 1103, and 1104 of FIG. 11) and long-axis (in case of three long-axis cine-MRI datasets: 1105, 1106, and 1107 of FIG. 11) cine MRI datasets are then put into each of the 16 AHA segments which correspond to their locations in the datasets.

Optionally, 3D strain can be computed based on the 2D short-axis cine-MRI dataset and long axis cine-MRI dataset. For the 3D strain computation reference is made to the flowchart of FIG. 10. Step 1001 and 1002 represents the retrieval of the short-axis cine MRI image dataset (FIG. 8, 808) and the long-axis cine MRI image dataset (FIG. 8, 805, and/or 806 and/or 807) respectively. The displacement field within the 2D cine-MRI image dataset is computed within step 1003 and 1004 as described previously. All extracted displacement information from the 2D MRI image datasets is converted into one 3D displacement model. This 3D process uses all the displacements or strain as previously described on the 2D cine MRI image datasets that is the displacements from short-axis and long-axis cine MRI. Within the short-axis and long-axis cine MRI image datasets, the image frames (all images in time, representing the cardiac cycle, within one slice) are organized by phase (trigger time) and for the short-axis cine MRI dataset the slices are sorted for instance from base to apex.

Within step 1005, for each image frame, the pixels inside the myocardial mask are translated into 3D, and those pixels represents the displacement vectors origin. The ends of the vectors are computed by adding the calculated displacement (from step 1003 and 1004) in x and y directions to the current pixel (still in 2D coordinate system) obtaining the position of the displaced pixel which is then also translated to 3D. This 3D transformation is done for each pixel within the volume of interest by translated to its 3D position by applying the following transformation matrix:

$$\begin{bmatrix} X \\ Y \\ Z \\ 1 \end{bmatrix} = \begin{bmatrix} U_x \Delta_u & V \Delta_v & 0 & P_X \\ U_y \Delta_u & V_y \Delta_v & 0 & P_y \\ U_y \Delta_u & V_z \Delta_v & 0 & P_z \\ 0 & 0 & 0 & 1 \end{bmatrix} \begin{bmatrix} u \\ v \\ 0 \\ 1 \end{bmatrix} \quad \text{eq. 7}$$

Figure 12:
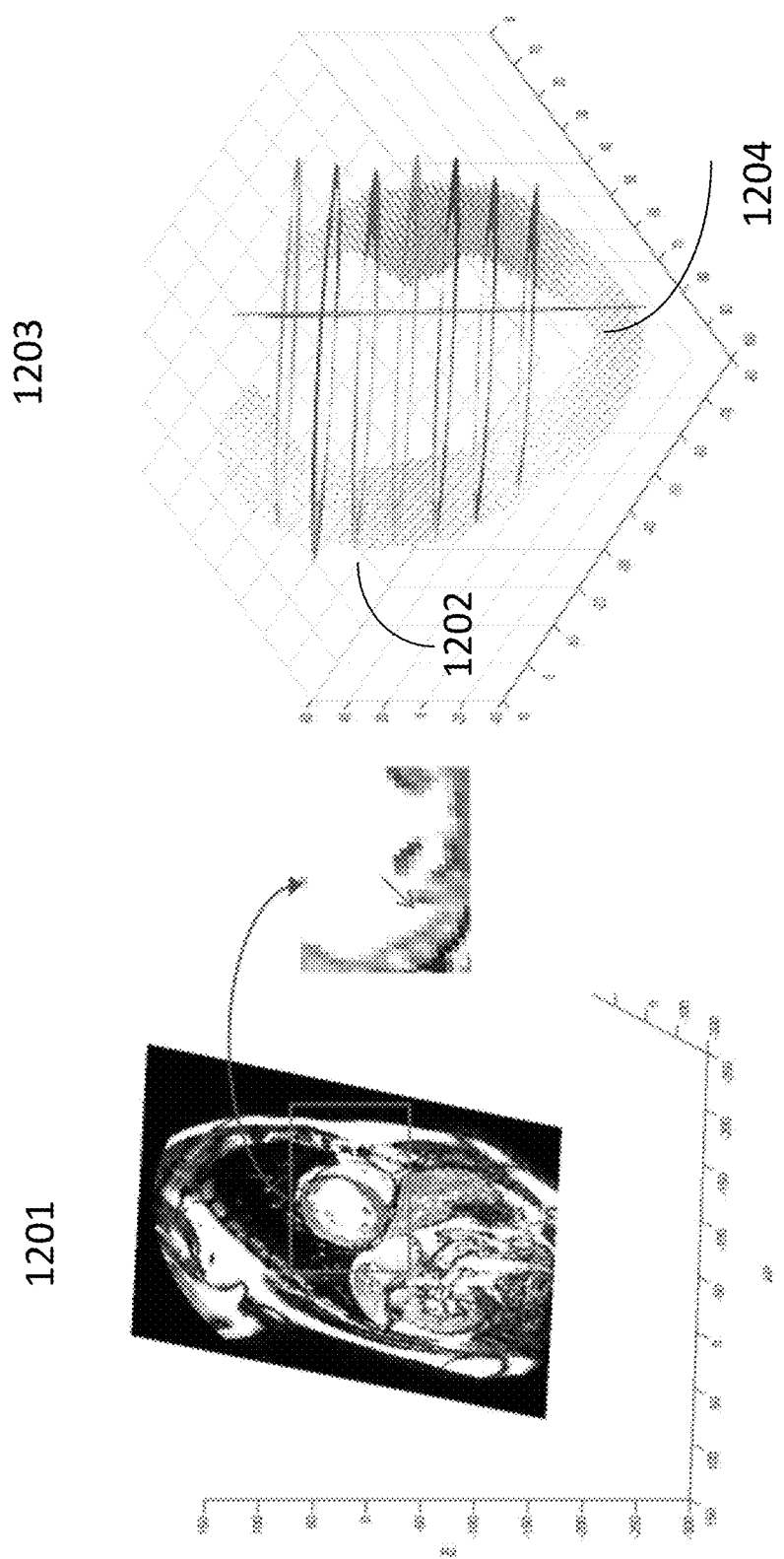
FIG. 12 shows one SA image frame visualized in 3D and the resulting 3D displacement.

(u,v)—2D image coordinate;

(x,y,z)—Transformed 3D coordinate;
(Px,Py,Pz)—Image Position, obtained from DICOM;
($U_{x,y,z}, V_{x,y,z}$)—Image Orientation, obtained from DICOM;
($\Delta_u, \Delta_v$)—Pixel spacing, obtained from DICOM In the FIG. 12, 1201 shows one short axis image frame visualized in 3D and the resulting 3D displacement field after applying the transformation of equation 7 by 1202. Within FIG. 12, 1203 represent a combination of all the displacement vectors resulting from the slices within the short-axis cine-MRI including the displacement vector resulting from one long-axis cine-MRI (1204).

To combine the obtained short and long axis displacements into one 3D displacement an interpolating method is used. This is achieved by creating an interpolating function using the data from the long axis view and then estimate the value of those displacements in the short axis positions. This is done since the short-axis covers the a larger part of the myocardium volume as compared to the long-axis dataset, on the other hand the short-axis datasets doesn't contain any information on longitudinal strain.

The interpolation function is based on a delaunay tetrahedrization interpolation method as for instance described by Amidror et al., "*Scattered data interpolation methods for electronic imaging systems: a survey*" J. Electron. Imaging 2202, vol. 11, no. 2: 157. Essentially this approach consists of two steps, first the scattered points are tetrahedrized using delaunay tetrahedrization, that is, a subdivision of the dataset volume into "pyramids" of various shapes and sizes, and then a local interpolation scheme is used within each tetrahedron, in other words the closet tetrahedron to the point in studies is used to perform a local interpolation.

The resulting vectors are then combined, for instance by averaging or by adding plurality of vectors components, resulting in a single displacement field containing information from the different left ventricle views.

Optionally, motion between the different cine-MRI image datasets, for instance due to respiratory and/or patient motion can be corrected for instance as thought by Slomka et al., "*Patient motion correction for multiplanar, multi-breath-hold cardiac cine MR imaging*", J. Magn. Reson. Imaging, vol. 25, no. 5, pp. 965-973, 2007. Briefly, Slomka et al. describes a process that computes the intersection between the 3D translated images, and applying a cost measure to determine the degree of correlation between them. One of the images is then iteratively moved in a certain range, in which, for each of the new positions in this range the intersection and cost measure between images is recalculated. The position which maximizes the correlation is then defined as the best image position.

Figure 10:
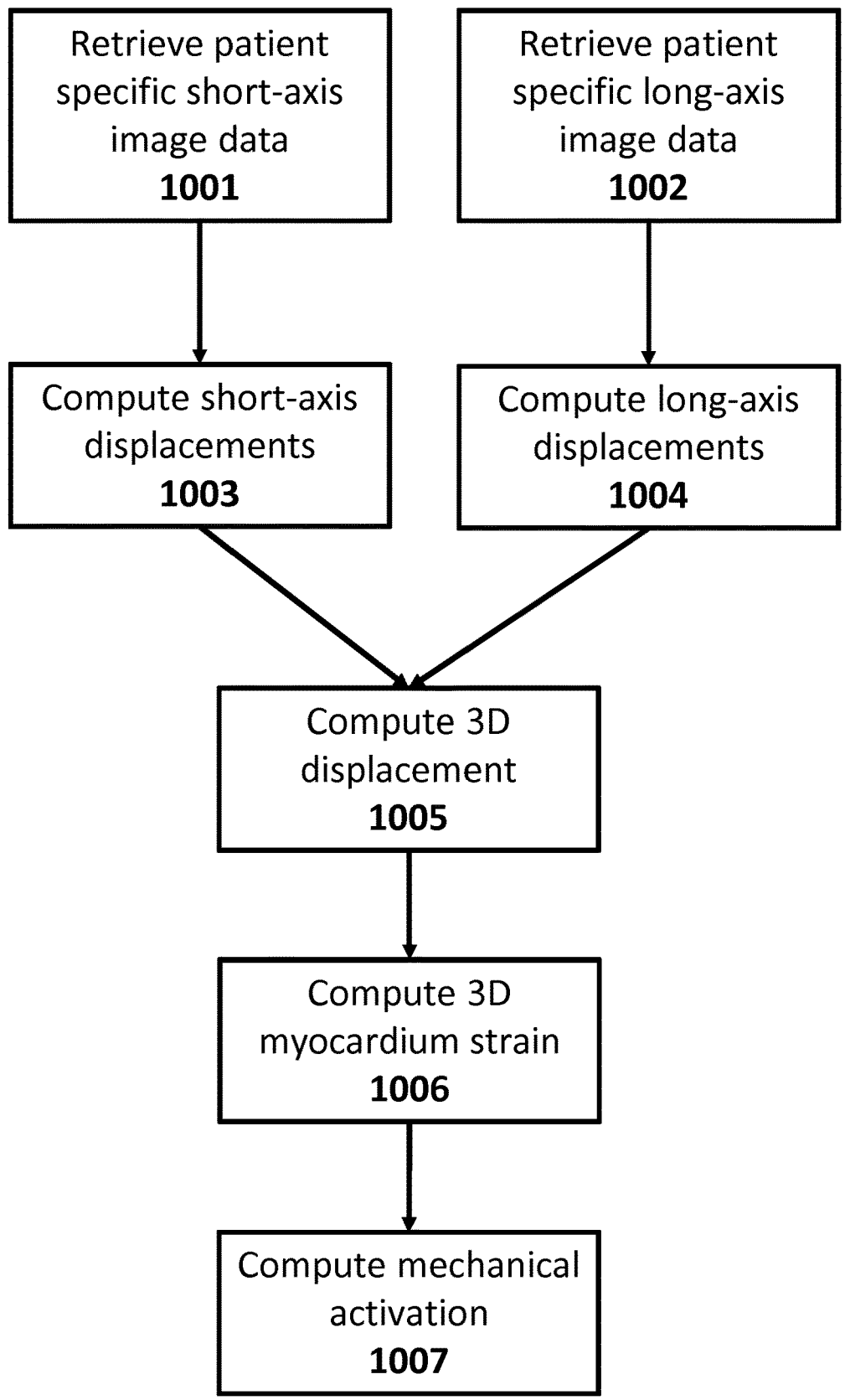
FIG. 10 shows a flowchart of a method for computing the mechanical activation.

Within step 1006 of FIG. 10, the 3D strain is calculated. Having the 3D displacement field as described by step 1005, similarly to the 2D process it is required to compute the spatial gradients of the displacement field. This can be done for instance by a Radial Point Interpolation Method (RPIM), as described by Liu et al., "*A meshfree radial point interpolation method (RPIM) for three-dimensional solids*", Comput. Mech. 2005, vol. 36, no. 6, pp. 421-430. The advantage of using a RPIM method is that this method allows the estimation of displacement field derivatives without the need of constructing a mesh. Instead the RPIM method computes the gradient analytically from a continuous and differentiable interpolant of the displacement field.

From the directional derivatives obtained from the previous step, the strain can be calculated using similar formula as the 2D strain but extended into the 3D domain. First, the deformation gradient tensor (F) is calculated using the following formula:

$$F = I + \begin{bmatrix} \frac{\partial D_x}{\partial x} & \frac{\partial D_x}{\partial y} & \frac{\partial D_x}{\partial z} \\ \frac{\partial D_y}{\partial x} & \frac{\partial D_y}{\partial y} & \frac{\partial D_y}{\partial z} \\ \frac{\partial D_z}{\partial x} & \frac{\partial D_z}{\partial y} & \frac{\partial D_z}{\partial z} \end{bmatrix} \qquad \text{eq. 8}$$

with $D_x$, $D_y$, and $D_z$ as the interpolants for displacement at x, y, and z direction, respectively and I as the identity matrix. Afterwards, the Green Cartesian strain tensor ($E_c$) is calculated using the following formula:

$$E_c = \frac{1}{2}(F^T F - 1) \qquad \text{eq. 9}$$

resulting in the following strain components:

$$E_c = \begin{bmatrix} E_{xx} & E_{xy} & E_{xz} \\ E_{yx} & E_{yy} & E_{yz} \\ E_{zx} & E_{zy} & E_{zz} \end{bmatrix} \qquad \text{eq. 10}$$

Figure 8:
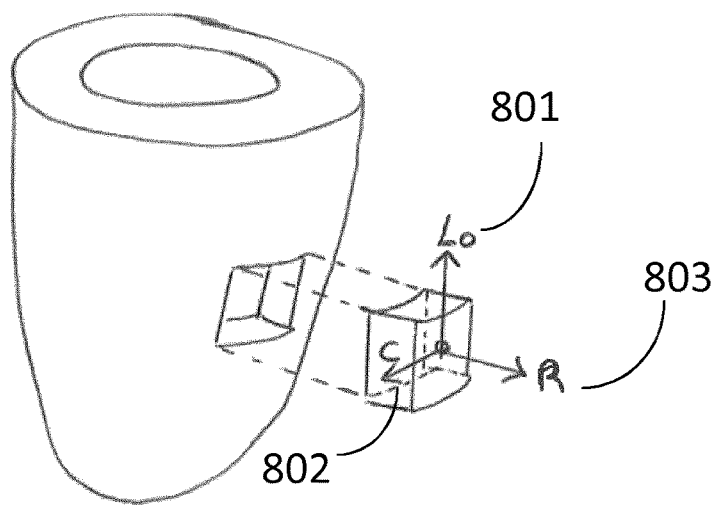
FIG. 8 shows the different principle direction of myocardium strain include some examples of different cine-MRI image datasets used to calculated myocardium strain.
Figure 8:
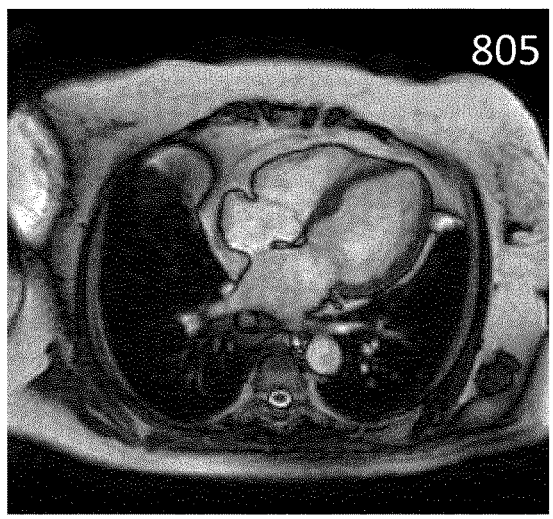
Figure 8:
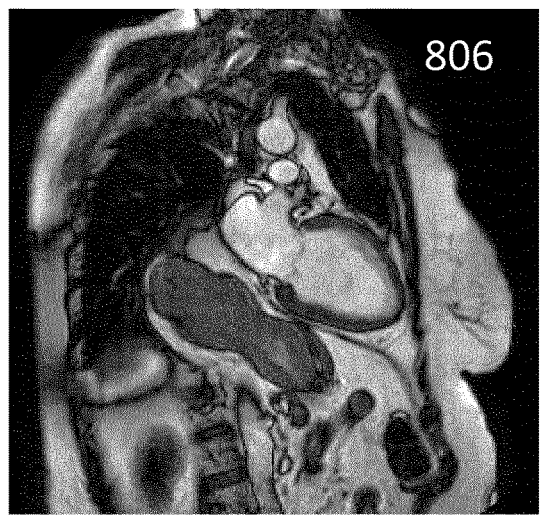
Figure 8:
Figure 8:

In order to properly characterize cardiac performance, the strain needs to be converted into local coordinate system of the heart, namely into radial, circumferential, and longitudinal strains (803, 802, and 801 respectively as shown in FIG. 8). An example method to perform the conversion is introduced by Suever, et al. in "*Right Ventricular Strain, Torsion, and Dyssynchrony in Healthy Subjects using 3D Spiral Cine DENSE Magnetic Resonance Imaging*", IEEE Transactions vol. 36, issue 5, 2017: pp. 1076-1085. In brief, the principal directions of the local coordinate system is determined based on the 3D geometry of the ventricle. First, the radial direction is defined as the vector normal to the ventricle surface pointing inside the ventricle. The longitudinal direction is defined as vector tangential to the surface, pointing to the apex. The circumferential direction is calculated as the cross product of the radial and longitudinal direction. These principal directions is put into a matrix R.

$$R = \begin{bmatrix} r_x & c_x & l_x \\ r_y & c_y & l_y \\ r_z & c_z & l_z \end{bmatrix} \qquad \text{eq. 11}$$

where r, c, and l are the vectors pointing to radial, circumferential, and longitudinal directions. Using the eq. 4 as basis, but extended into 3D domain, the following strain in local coordinate system is obtained:

$$E_p = \begin{bmatrix} E_{rr} & E_{rc} & E_{rl} \\ E_{cr} & E_{cc} & E_{cl} \\ E_{lr} & E_{lc} & E_{ll} \end{bmatrix} \qquad \text{eq. 12}$$

where diagonal components: $E_{rr}$, $E_{cc}$, and $E_{ll}$ are the radial, circumferential, and longitudinal strains, respectively.

Figure 13:
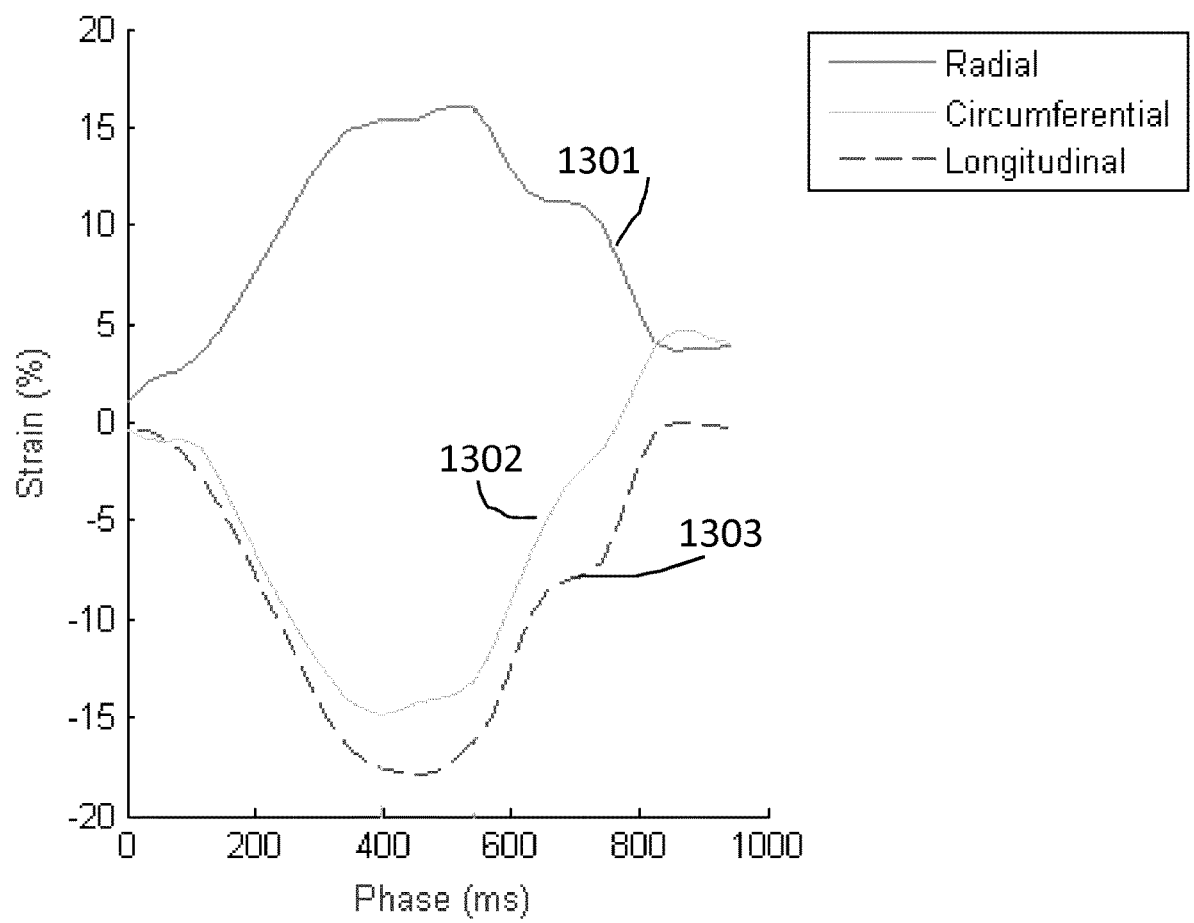
FIG. 13 shows a graph of the global radial, circumferential, and longitudinal strain within one cardiac cycle.
Figure 14:
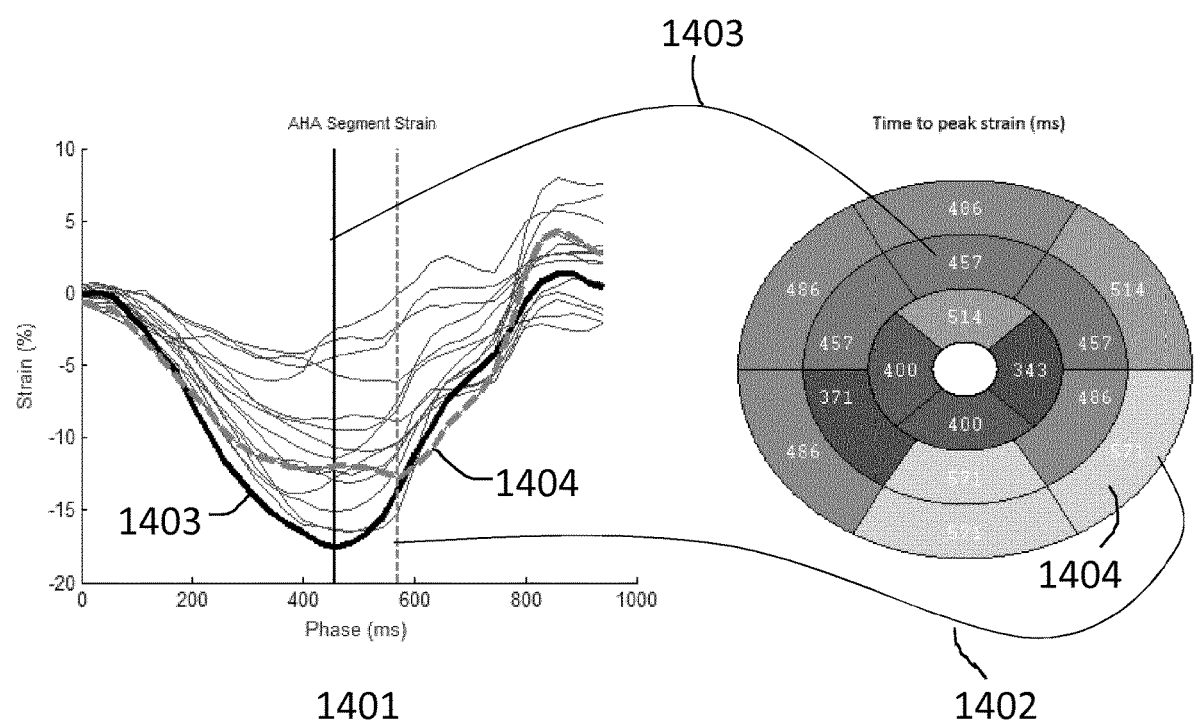
FIG. 14 visualize the methodology for creation of the mechanical activation map using latest activation and represented in 16-segment AHA model.

The strain analysis contain the cardiac deformation information over the whole cardiac cycle. This information can be presented for instance as a curve plot of the strain values over time (FIG. 13). FIG. 13, shows a graph of the global radial (1301), circumferential (1302) and longitudinal strain (1303) within one cardiac cycle (x-axis represent the cardiac time in case of heart frequency of 60 beat per minute). The global strain is calculated as the average strain values at each position. From the calculated strain, within step 1007 of FIG. 10, the mechanical activation information over the whole cycle can be calculated, for instance the mechanical activation delay. An example on how to calculate mechanical activation delay is by locating the time where the strain curve shows maximal (absolute) strain, or also known as peak strain. Since the 3D strain information of various segments and parts of the heart is available, the mechanical activation information of various segments and parts of the heart can be calculated. From this mechanical activation information of various segments and parts of the heart, the heart segment or part that experience the latest mechanical activation can be located. An example on how to present this information is by present it in accordance with the 16 AHA segments model, where the strain curve (radial, longitudinal, circumferential, or the 3D strain vector) of each AHA segment is made available (1401 in FIG. 14). The information presented is for instance the timing when the peak strain occurred at each segment (1402 in FIG. 14). Plurality of segment that shows the latest peak strain is for instance regarded as the segment that experienced the latest mechanical activation. An example is shown in FIG. 14, where AHA segment 7 (1403 in FIG. 14) shows earlier time to peak strain, while AHA segment 5 (1404 in FIG. 14) shows the latest time to peak strain. Therefore, in this example AHA segment 5 is regarded as one of the segments that experience latest mechanical activation.

Figure 15:
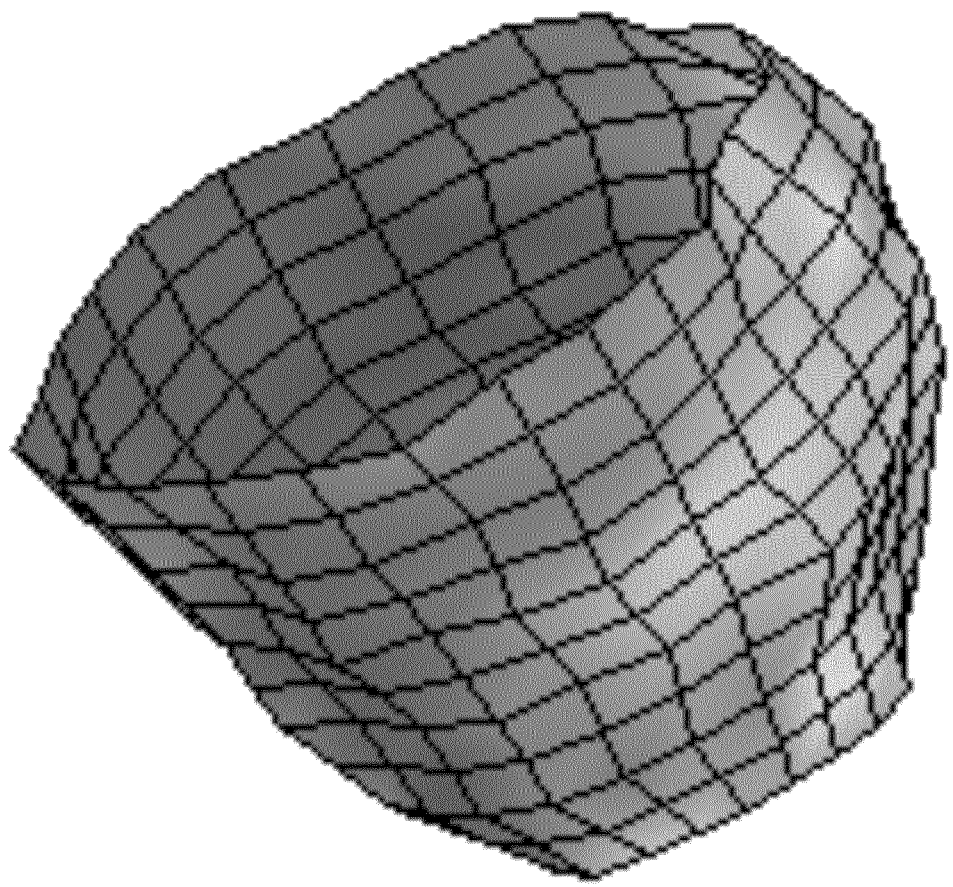
FIG. 15 shows the mechanical activation color encoded on a 3D surface model.

Another example on how to present the mechanical activation information is by visualizing it in a 3D surface model. The 3D surface model can be marked for instance by color-coding parts of the model corresponding to their mechanical activation delay (as described by the previous step), where for instance part with highest mechanical activation delay is given lighter color shade (FIG. 15). Therefore, in this example, the region of the 3D surface model with lighter color shade is regarded as the part with the latest mechanical activation (1501 in FIG. 15).

Figure 16:
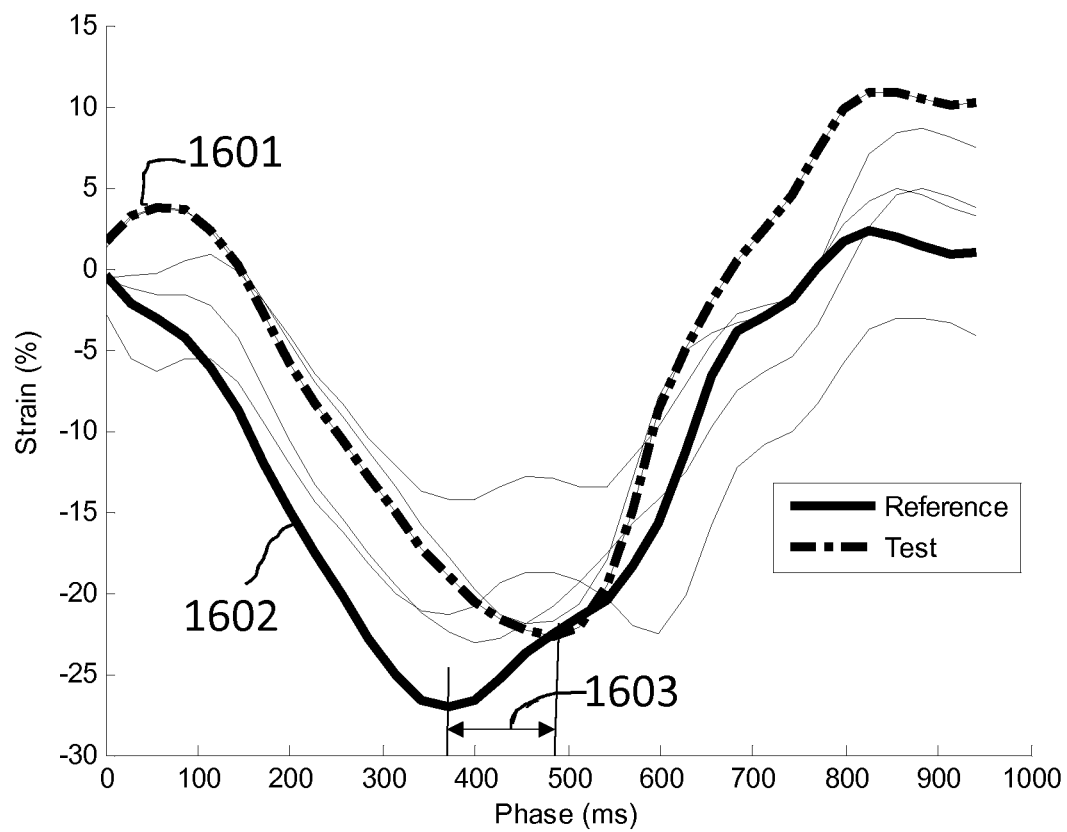
FIG. 16 visualize the methodology for creation of the mechanical activation map using cross-correlation of TDC curves.

Another example on how to calculate mechanical activation delay is presented by Mischi, et al. in *"Three-dimensional quantification of regional left-ventricular dyssynchrony by magnetic resonance imaging"* in Conf Proc IEEE Eng Med Biol Soc 2011: pp. 2646-2649. In brief, each of the mechanical activity pattern curves is compared to the subject-specific reference curve. An example on the comparison method is by use of cross-correlation between the test curve (1601 in FIG. 16) and the reference curve (1602 in FIG. 16). By use of this comparison, the timing difference between the test curve and the reference curve is obtained (1603). An example on how to finally calculate the mechanical activation delay is by comparing the timing differences of each test curve to the first moving segment. Above method of Mischi et al. relies on time displacement curves (TDC), computed from the radial endocardial motion pattern within each cine-MRI short-axis slice. The radial endocardial motion patterns is computed as the distance between the centroid of the LV blood pool and each of the points on the endocardial border (for instance 360 point equally spaced) during the cardiac cycle. After cross-correlation all the TDC with an identified reference TDC, the delay is calculated and the tissue synchronization index (TSI) can be expressed as the standard deviation of the TDC delay times. The calculated TDC delay does not represent the true mechanical delay, since the delay is computed relative to the reference TDC. To establish the mechanical delay, the delay computed needs to be related to the start of the cardiac cycle. This is accomplished by using the trigger time of each frame combined with the delay resulting from the cross correlation. Optionally, by including the long-axis cine-MRI dataset(s) would improve the identification of the reference TDC by determining the contraction time on the long-axis cine-MRI dataset(s) and integrating this information at determination of the TDC of each short-axis slice. Optionally, the delay is expressed in percentage of the cardiac cycle.

In step 105 of FIG. 1, the 3D roadmap model is created. This roadmap can be used as pre-procedural planning of the CRT procedure, as input for the guidance during a CRT procedure as described below with reference to FIG. 18, or as guidance during a CRT procedure in combination with EAM.

The 3D roadmap model is a 3D model which incorporates several anatomical 3D geometries including quantitative information which is visualized as a parametric overlay on the 3D model. The quantitative information includes myocardium scar distribution (FIG. 1, 103) including mechanical activation (FIG. 1, 104) visualized for example as a parametric overlay on the 3D anatomical structure as for instance the 3D surface of the LV endocardial or epicardial model. A parametric overlay is a method to visualize location specific quantitative results, as for instance the results resulting from equation 13 by different color or grey tones at the corresponding location. In which the color or grey tone represent the specific quantitative value at that specific spatial location. The 3D roadmap can be created in several ways. The method of choice strongly depends on the aim for guidance as described above.

The first method, with focus on pre-procedural planning of the CRT procedure, uses the full 3D anatomical geometry resulting from step 102 (FIG. 1), and an example is shows by 508 (FIG. 5). This means all 3D cardiac structures are represented, as well as the 3D infarct geometry. In such an example, the 3D epicardial geometry is preferable transparent visualized. Next, the calculated myocardium scar distribution as a result of step 103 of FIG. 1 is weighted with the calculated mechanical activation (step 104 of FIG. 1) before superimposing this weighting results as for instance a color or grey value overlay on the endocardial 3D geometry or the epicardial 3D geometry. The weighting can be a linear or a non-linear weighting. For instance, the linear weighting can be accomplished by equation 13:

overlay value=$\alpha$*(1−final myocardium scar distribution)*$\beta$*mechanical activation where final myocardium scar distribution is the result of equation 0 and normalized between 0 and 1 and mechanical activation the result of step 104 of FIG. 1. Like previously mentioned, placement of the LV lead can be done either endocardial or epicardial (inside a coronary vein). Therefore the physician is able to choice to map this color overlay either on the endocardial 3D geometry or on the epicardial 3D geometry. This will allow flexibility on planning the CRT procedure and allow the physician to make the best choice for the patient of interest. Furthermore, the physician is able to rotate, zoom and pan the 3D roadmap model allowing detailed examination of specific region of interest (for instance infarct tissue, difference in mechanical activation) for optimal pre-procedural planning.

Figure 17:
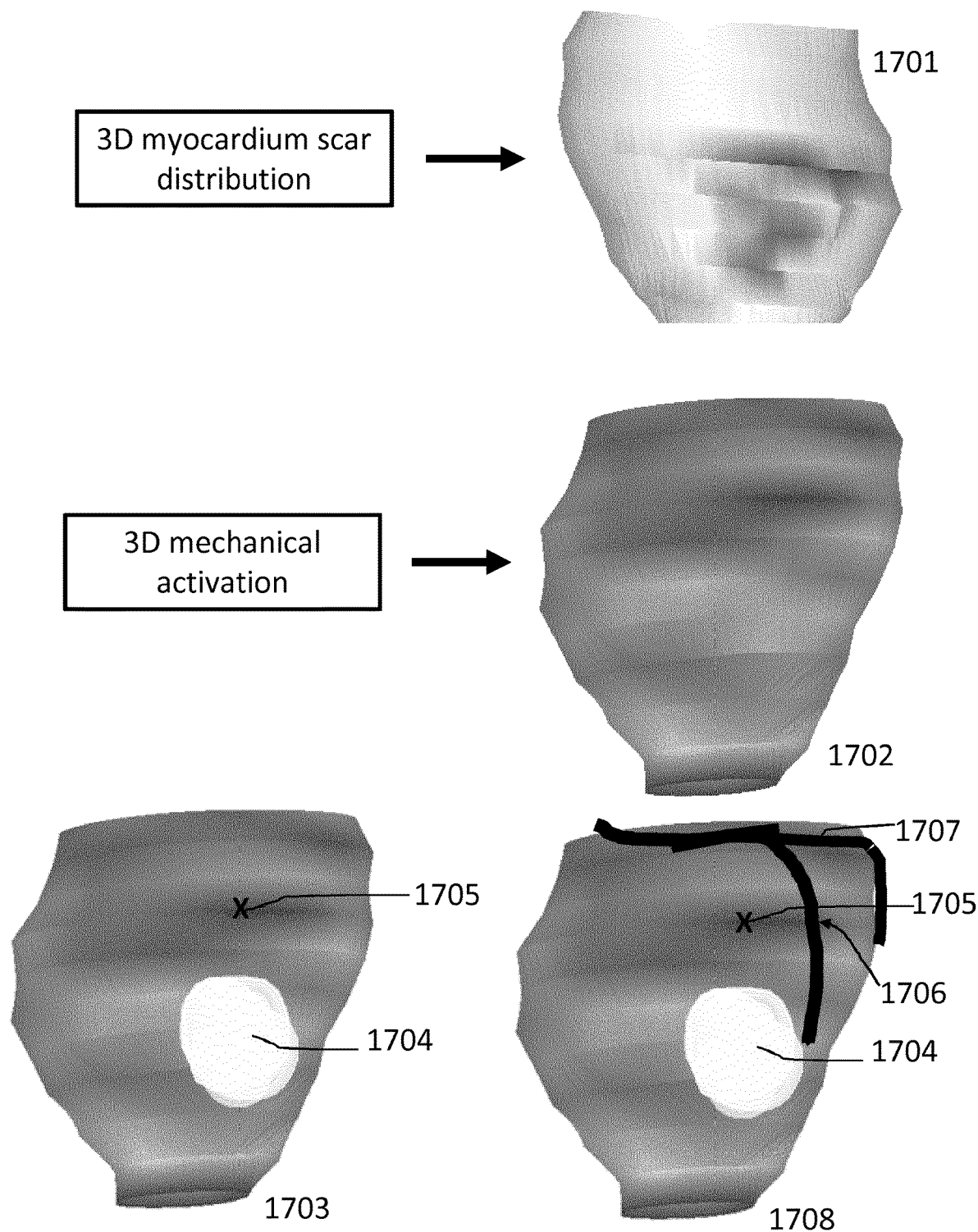
FIG. 17 shows an example of the 3D roadmap creation.

The second method, with focus on guidance during a CRT procedure (as described below with reference to FIG. 18) uses a 3D cardiac model and includes optionally the 3D coronary vein geometry and/or 3D phrenic nerve geometry. This 3D cardiac model is either based on the 3D LV endocard or LV 3D epicardial, and optionally RV endocard, coronary vein and/or phrenic nerve, and depends on either endocardial or epicardial LV lead placement strategy as described before. An example us such a 3D roadmap creation is presented by FIG. 17. Within FIG. 17, 1701 shows the 3D myocardium scar distribution, as the result from step 103 of FIG. 1, superimposed as a color or grey value overlay on the 3D endocardial geometry. In this example, white represents no myocardium infarct and black represents severe myocardium infarct resulting from equation 0. Please note that within this example, the parameters used within equation 0 are chosen for endocardial LV lead placement. The 3D mechanical activation, as a result of step 104 of FIG. 1 is superimposed as a color or grey value overlay on the 3D endocardial geometry (FIG. 17, 1702). In this example (1702), white represent short mechanical activation delay and black long mechanical activation delay. Next, both 3D representations 1701 and 1702 are merge into one 3D roadmap model represented by 1703. In this example, the white spot (1704) represents the infarcted myocardium region and an optimal LV lead location would be the location which darkest color (represented by the 'X', 1705). As described before, optimal LV lead placement position is defined as the region with the latest electrical activation (and since mechanical activation correlates with electrical activation, mechanical activation is used) which is free from myocardium scar. For epicardial LV lead placement strategy, the LV lead is placed inside a coronary vein. To provide information on the feasible locations, visualization of the 3D coronary vein geometry allows assessment of feasible LV lead locations. FIG. 17, 1708 shows the same figure as 1703, but now the 3D coronary vein geometry is included in the 3D roadmap model (1707). As noticeable, the optimal LV lead location (1705) cannot be reached by an epicardial LV lead placement strategy since no coronary vein is overlapping this region. The most optimal LV lead placement position would now be 1706, which is free from myocardium scar, the latest mechanical activation and assessable through the coronary vein. Optionally, the 3D phrenic nerve geometry is included or incorporated in the color overlay and representing a value which is the least optimal (in example 1703 or 1708, the lightest color (1704)). Also this method is described with focus for guidance during the CRT procedure, the described 3D roadmap visualization can also be used as a pre-procedural to assist the physician in optimal treatment strategy.

The third method is focused on guidance during a CRT procedure in combination with EAM. In this situation, the 3D roadmap model is registered with the 3D EAM model and this registered model is used during the CRT procedure to guide in optimal LV lead location. For this purpose, the geometry of the coronary sinus as presented within FIG. 4B, 414 is preferably used to perform the registration with 3D EAM. The 3D roadmap model can be either as described above from the first method or the second method or any combination thereof.

The fourth method is focused on providing a method to improve patient selection criteria for patients who receive CRT. For instance, patient with a LBBB are known to benefit the most from CRT. LBBB result in a desynchronized contraction of the hearth; left ventricle shows a delayed contraction as compared to the right ventricle. This can be assessed by quantification of the mechanical activation along the LV myocardium and superimposed as parametric overlay on either the LV endocardial surface or LV epicardial surface. As described in step 104 of FIG. 1, either myocardium strain can be used as well as the calculated TDC delays or TSI. Optionally, myocardium scar distribution as calculated within step 102 of FIG. 1 can be incorporated into the parametric overlay as for instance described by equation 13.

Furthermore, the 3D roadmap is not limited to the described four methods in this section, any combination of the available information can be used to create the 3D roadmap. Furthermore, the user is allowed to change the parameters in the different equations (e.g. equation 0, equation 13) which allows enhanced insights in the underlying myocardium condition. For instance, as described before, myocardium ischemia may be identified separately to consider a PCI procedure before performing a CRT procedure. Another example would be to assess in more detail types of myocardium infarct as described before with reference to FIG. 6.

Figure 18:
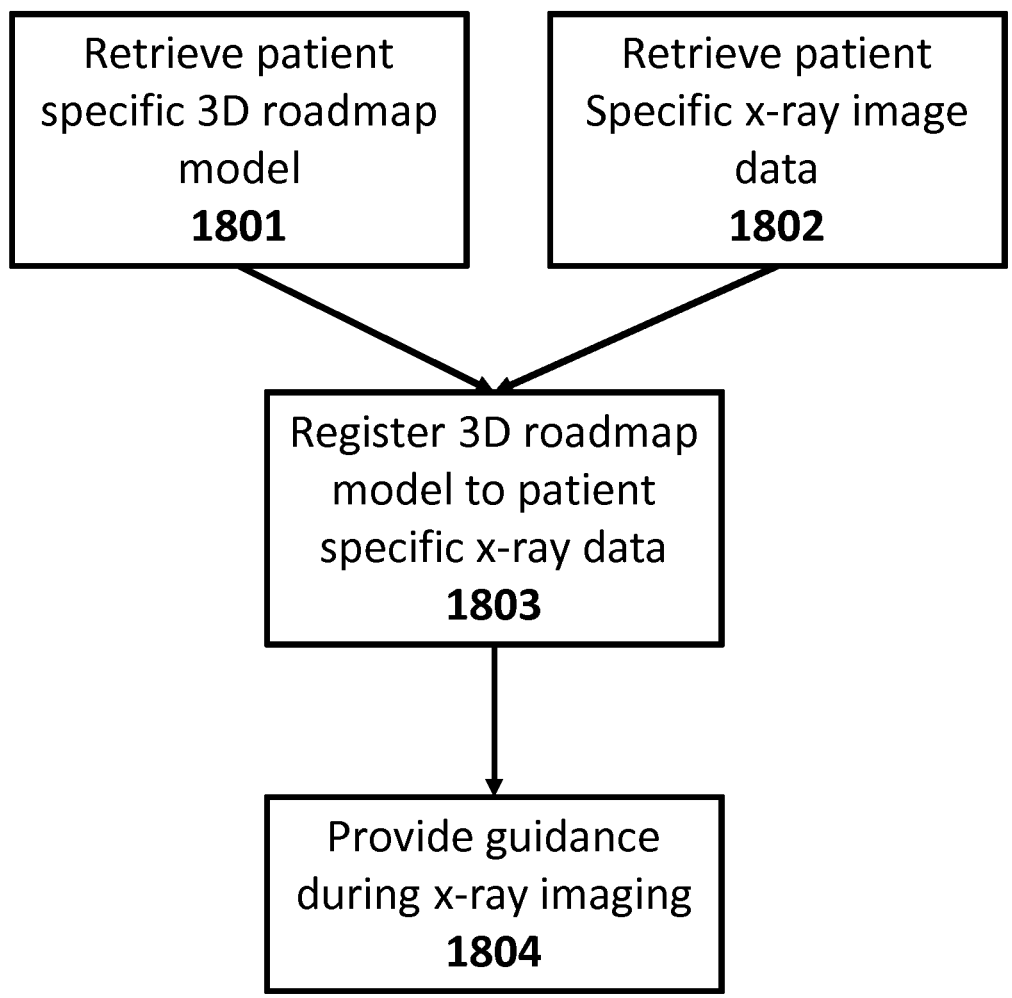
FIG. 18 shows a flowchart of the steps of the invention in another preferred embodiment.

An embodiment is now disclosed with reference to FIG. 18. The therein-depicted operations can, obviously, be performed in any logical sequence and can be omitted in parts. The objective of the embodiment as presented in FIG. 18 is to provide guidance during the CRT procedure supporting the physician (e.g. electrophysiologist) in optimal LV lead treatment strategy (e.g. optimal LV lead position).

First, the patient specific 3D roadmap model (1801) is retrieved. This patient specific roadmap model can be generated as described by the steps within FIG. 1. Besides the patient specific 3D roadmap model, patient specific x-ray image data as obtained during the CRT procedure is retrieved (1802). This can be an x-ray venogram, meaning an x-ray angiographic image sequence in which the contrast liquid is injected in the coronary sinus, or an x-ray image without contrast liquid, further reference to as fluoroscopic x-ray image dataset. In both cases, the x-ray image dataset normally consists of multiple image frames over time, and in case of guidance (1804) real time x-ray image data. This guidance is normally provided on the real time fluoroscopic x-ray image dataset. Although, guidance can also be provided on the real-time x-ray venogram on a retrieved x-ray mage data for instance from a PACS or VNA.

The next step (FIG. 18, 1803) involves registration the patient specific 3D roadmap model to the x-ray venogram. Preferable the image frame within the x-ray venogram corresponding to the cardiac phase in which the patient specific 3D model is created is selected for the registration process. Knowing the geometry of the x-ray system (such as rotation, angulation, magnification) the 3D model is projected on the 2D x-ray venogram as for instance taught by Lay, "*Linear algebra and its applications*", 2012, 4th edition, p 142-143, Addison-Wesley Longman. Knowledge on the location of the wire positioned at the RV-apex (FIG. 19, 1902) and/or RV atrium (FIG. 19, 1901) can be used to guide the registration process. In case the patient specific 3D roadmap model includes the geometry of the coronary veins, the veins visible in the x-ray venogram (FIG. 19, 1903) can be used as well to guide the registration process.

In step 1804 of FIG. 18, guidance is provided to the physician. The outcome of step 1803 results in a so called static aligned overlay. The presented overlay, superimposed on the x-ray image dataset, can be presented in several ways to the physician. For instance, the cardiac structures (RV chamber, LV chamber, infarct and/or coronary vein) can each be superimposed on the x-ray image dataset using different colour with or without transparency. Additionally, the mechanical activation (FIG. 1, 104) with or without the myocardium infarct distribution (FIG. 1, 103) using equation 13, can also be colour coded and/or optimal lead position can be emphasized using a distinguished colour.

Furthermore, a distinction can be made between the front and the back of the patient specific 3D roadmap model by for instance only showing the front side of the 3D roadmap model to the physician or by assigning a different color map to the front side of the 3D roadmap model as opposed to the back side. Optionally also different grades of opacity can be applied to distinguish between the front and the back side of the patient specific 3D roadmap model.

Optionally, the static aligned overlay can be adjusted to dynamically follow breathing motion of the patient. To be able to do so, the movement of one of the guidewires in the x-ray venogram (for instance the wire positioned at the RV-apex (FIG. 19, 1902) and/or RV atrium (FIG. 19, 1901)) is tracked. This can be done for instance by automatically detecting the guidewire tip, the RV apex lead or the RV atrium lead in one of the image frames of the x-ray venogram. A template can then be made of a region containing the guidewire tip. This template can then be used on subsequent image frames of the x-ray venogram to obtain the displacement of the guidewire in each frame relative to the first image frame, thus yielding a displacement pattern. The displacement pattern of the wire contains both cardiac as well as breathing motion. The low frequency term of the displacement pattern corresponds to the breathing motion of the patient. This low frequency section of the displacement pattern can then be applied to the static aligned overlay, resulting in an overlay that dynamically moves with the breathing motion of the patient.

Even more optionally, the cardiac motion of the patient can also be taken into account while registering the patient specific 3D roadmap. From the cine-MRI dataset the 3D displacement of the myocardium is computed as described in step 1005. This information can be used to deform the 3D roadmap model, yielding in a 3D roadmap model over time. Each deformed 3D roadmap model has a direct relation to the ECG signal, therefore the corresponding deformed 3D roadmap model can be chosen belonging to the cardiac phase at which the image frame of the x-ray venogram has been acquired. An alternative approach to deform the 3D roadmap model is by computing the 3D deformation of the cardiac chambers based on the segmentation of the cardiac chambers within the cine-MRI image dataset.

Figure 19:
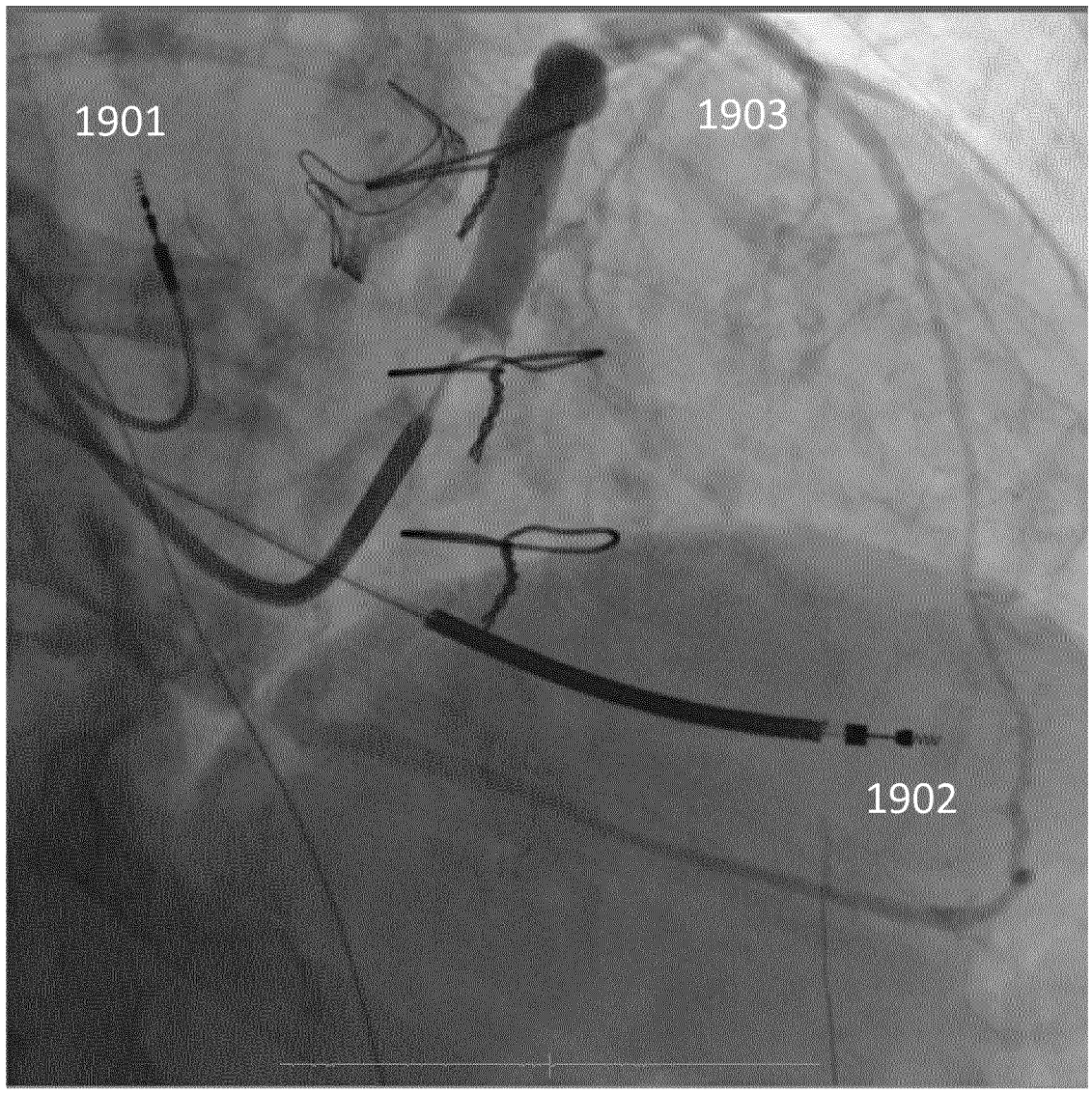
FIG. 19 shows an example of an x-ray venogram.

Alternatively, guidance can also be performed using the veins present in the x-ray venogram based on the method as taught by U.S. Pat. No. 9,256,936, "Method and apparatus for tracking objects in a target area of a moving organ". This method can for instance be done by tracking the movement of one or more features that are visible in the patient specific x-ray venogram and have the same periodic movement pattern as the object of interest. Examples of trackable features include anatomical structures such as contrast filled veins and interventional tools such as guide wires. In the real time fluoroscopic x-ray image dataset, two wires are present, one in the right atrium (FIG. 19, 1901) and one in the apex of the right ventricle (FIG. 19, 1902). The movement of these features are typically due to periodical motion originating from the heart beat and breathing motion. Because the motion of the veins and the guidewires is governed by the same source, the phase of the motion is synchronized at all times. When one of the features is obscured (for instance lack of contrast in the veins), knowledge about the periodic motion patterns of both features, the position of one of the features and the phase of the periodic motion can be used to derive the position of the obscured feature. First the position of the contrast filled veins and the guidewire is defined by the user. Once the position of the features is known, the system can acquire templates that capture the visual characteristics of the features. These templates can then be used to recognize the features in other frames. When feature obscuration is detected, indirect feature tracking is used. The position of the guidewire is the used together with the phase of the periodic motion and the dynamic geometric relation between the guidewire and the veins. By determining the position of the veins during a cardiac cycle relative to the position of the veins during the registering step 1803 of FIG. 18, the position of the 3D roadmap model can accordingly be adjusted to follow the same motion pattern throughout the cardiac cycle.

A technical effect of at least one embodiment is the ability to guide the movement and placement of a guide wire and/or catheter or other foreign object using (results of) two imaging modalities at the same time. One imaging modality may be X-ray fluoroscopy in which a bolus of contrast agent is introduced so that the coronary veins may be imaged and displayed. The other imaging modality may be magnetic resonance wherein the created patient specific 3D roadmap is used as guidance on the X-ray image data through registration with respect to each other. The operator may then utilize both the X-ray image and the magnetic resonance based 3D roadmap to advance the guide wire.

Figure 20:
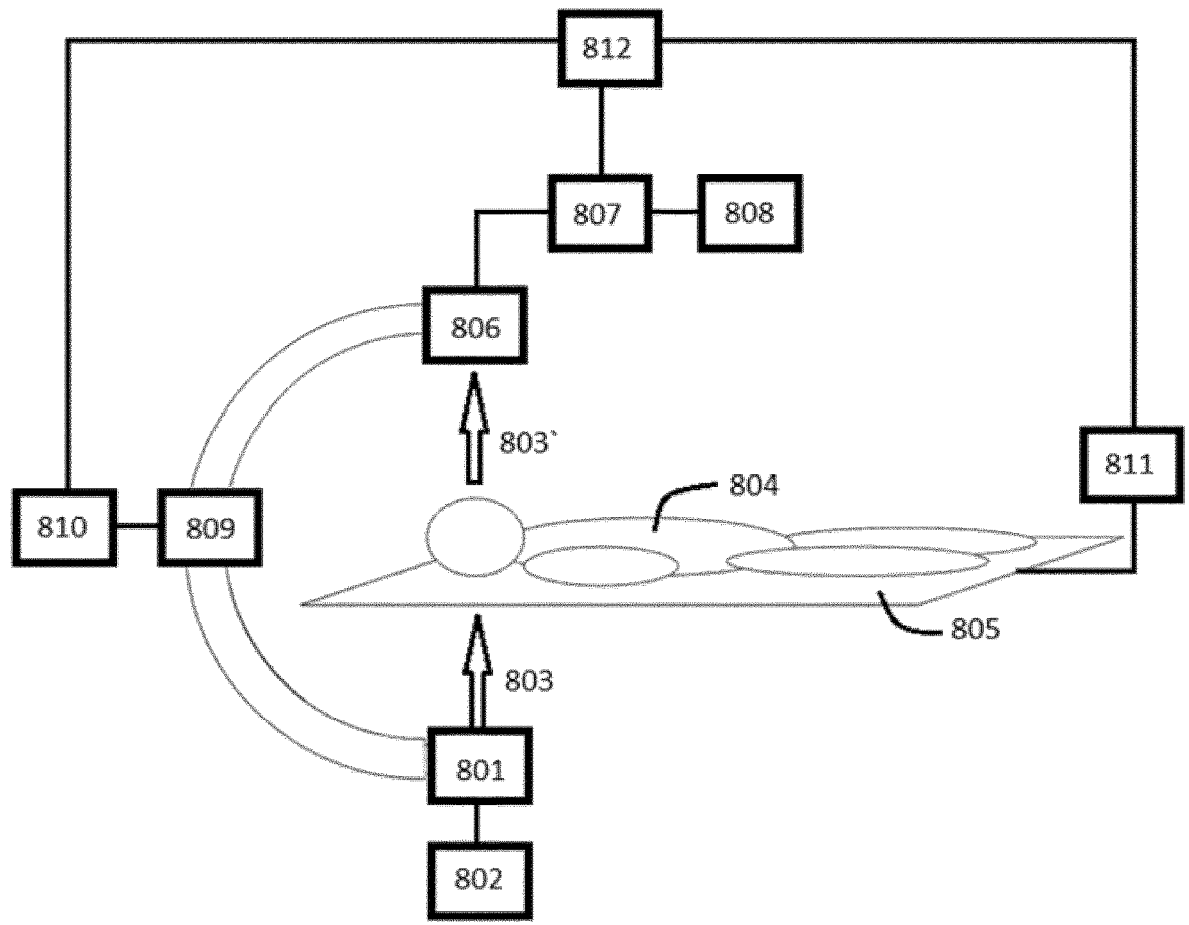
FIG. 20 shows an example of an x-ray cinefluorographic unit block diagram in accordance with an embodiment herein.

This one embodiment can be used on a standalone system or included directly in, for instance, an x-ray fluorographic system or any other image system to acquire two dimensional angiographic images. FIG. 20 illustrates an example of a high-level block diagram of an x-ray cinefluorograpic system. In this block diagram the embodiment is included as an example how the embodiment could integrate in such a system.

Portions of the system (as defined by various functional blocks) may be implemented with dedicated hardware, analog and/or digital circuitry, and/or one or more processors operating program instructions stored in memory.

The X-ray system of FIG. 20 includes an X-ray tubes 801 with a high voltage generator 802 that generates an X-ray beam 803. The high voltage generator 802 controls and delivers power to the X-ray tube 801. The high voltage generator 802 applies a high voltage across the vacuum gap between the cathode and the rotating anode of the X-ray tube 801.

Due to the voltage applied to the X-ray tube 801, electron transfer occurs from the cathode to the anode of the X-ray tube 801 resulting in X-ray photon generating effect also called Bremsstrahlung. The generated photons form an Xray beam 803 directed to the image detector 806.

An X-ray beam 803 consists of photons with a spectrum of energies that range up to a maximum determined by among others the voltage and current submitted to the X-ray tube 801.

The X-ray beam 803 then passes through the patient 804 that lies on an adjustable table 805. The X-ray photons of the X-ray beam 803 penetrate the tissue of the patient to a varying degree. Different structures in the patient 804 absorb different fractions of the radiation, modulating the beam intensity.

The modulated X-ray beam 803' that exits from the patient 804 is detected by the image detector 806 that is located opposite of the X-ray tube. This image detector 806 can either be an indirect or a direct detection system.

In case of an indirect detection system, the image detector 806 consists of a vacuum tube (the X-ray image intensifier) that converts the X-ray exit beam 803' into an amplified visible light image. This amplified visible light image is then transmitted to a visible light image receptor such as a digital video camera for image display and recording. This results in a digital image signal.

In case of a direct detection system, the image detector 806 consists of a flat panel detector. The flat panel detector directly converts the X-ray exit beam 803' into a digital image signal.

The digital image signal resulting from the image detector 806 is passed through a digital image processing unit 807. The digital image processing unit 807 converts the digital image signal from 806 into a corrected X-ray image (for instance inverted and/or contrast enhanced) in a standard image file format for instance DICOM. The corrected X-ray image can then be stored on a hard drive 808.

Furthermore, the X-ray system of FIG. 20 consists of a C-arm 809. The C-arm holds the X-ray tube 801 and the image detector 806 in such a manner that the patient 804 and the adjustable table 805 lie between the X-ray tube 801 and the image detector 806. The C-arm can be moved (rotated and angulated) to a desired position to acquire a certain projection in a controlled manner using the C-arm control 810. The C-arm control allows for manual or automatic input for adjustment of the C-arm in the desired position for the X-ray recording at a certain projection.

The X-ray system of FIG. 20 can either be a single plane or a bi-plane imaging system. In case of a bi-plane imaging system, multiple C-arms 809 are present each consisting of an X-ray tube 801, an image detector 806 and a C-arm control 810.

Additionally, the adjustable table 805 can be moved using the table control 811. The adjustable table 805 can be moved along the x, y and z axis as well as tilted around a certain point.

A general unit 812 is also present in the X-ray system. This general unit 812 can be used to interact with the C-arm control 810, the table control 811 and the digital image processing unit 807.

An embodiment of the invention is implemented by the X-ray system of FIG. 20 as follows. A clinician or other user acquires an X-ray angiographic image of a patient 804 at a certain projection by using the C-arm control 810 to move the C-arm 809 to a desired position relative to the patient 804. The patient 804 lies on the adjustable table 805 that has been moved by the user to a certain position using the table control 811.

The X-ray image is then generated using the high voltage generator 802, the X-ray tube 801, the image detector 806 and the digital image processing unit 807 as described above. This image is then stored on the hard drive 808. Using this X-ray image, the general processing unit 812 then registers the 3D roadmap model with the x-ray venogram and provides the user with guidance for positioning of the LV lead.

Figure 21:
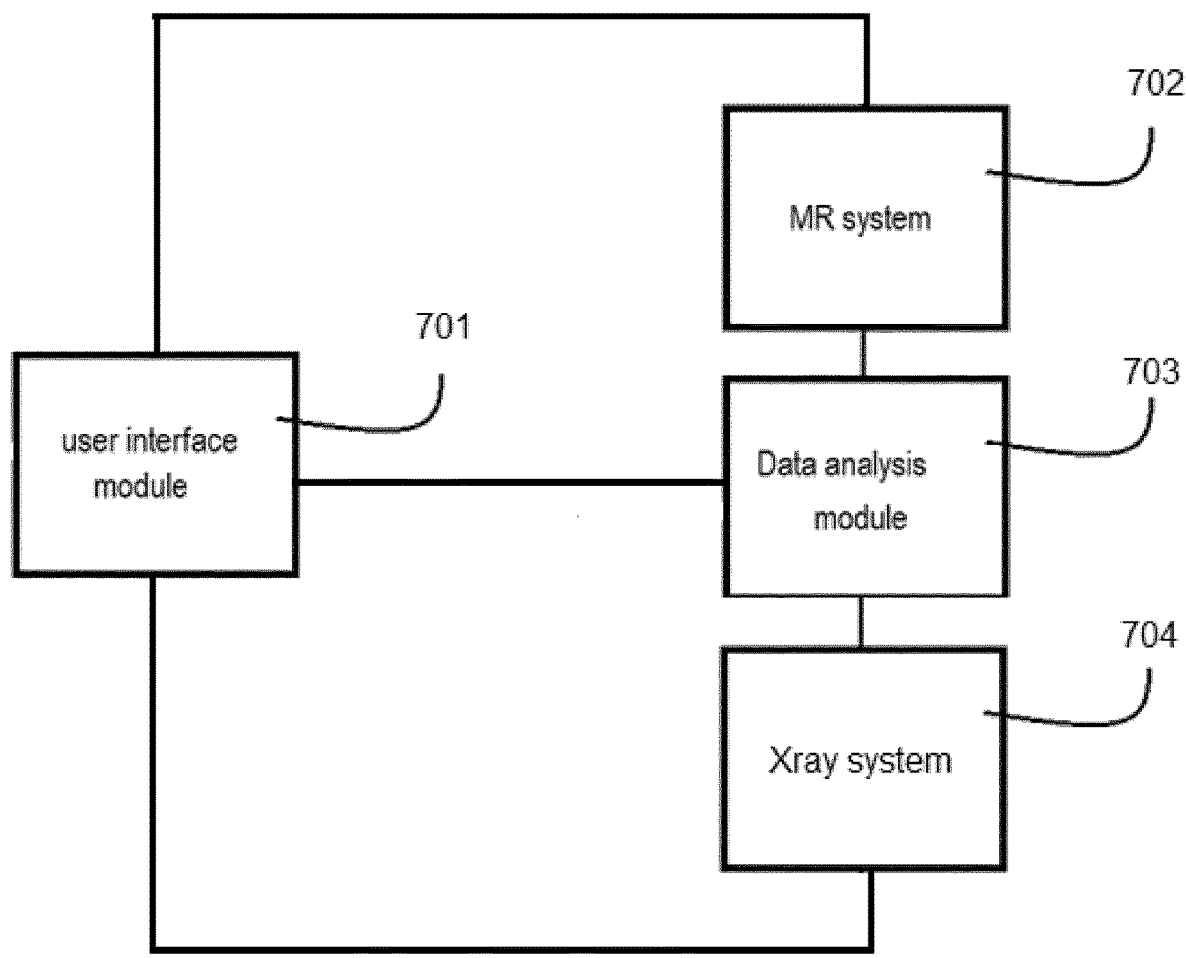
FIG. 21 shows a functional block diagram of an exemplary single plane angiographic system.

The relation between the MR and the X-ray system is shown in FIG. 21.

There have been described and illustrated herein several embodiments of a method and apparatus for providing information to the physician to support pre-procedural and peri-procedural CRT procedure. While particular embodiments of the invention have been described, it is not intended that the invention be limited thereto, as it is intended that the invention be as broad in scope as the art will allow and that the specification be read likewise. For example, the data processing operations can be performed offline on images stored in digital storage, such as a PACS commonly used in the medical imaging arts. It will therefore be appreciated by those skilled in the art that yet other modifications could be made to the provided invention without deviating from its spirit and scope as claimed. Another example, is that the invention can be utilized for patients suffering from ventricular tachycardias. Ventricular tachycardias is a type of cardiac arrhythmia which also arise from improper electrical activity, but now originating from the lower pumping chambers of the heart. One of the treatment option for ventricular tachycardias is catheter ablation therapy. This procedure targets the origin of the ventricular tachycardias by placing a long, thin wire or catheter into the heart chambers through the veins of the leg. When areas that are critical to the arrhythmia are identified, a localized delivery of radiofrequency energy is applied, which produces a small burn about 4 to 5 mm in diameter. The number of burns required to treat the VT varies among patients. In patients with scar tissue in the heart, ablations may be performed within the scar and around its perimeter to cauterize or ablate the abnormal electric circuit responsible for the ventricular tachycardias. Especially for planning the catheter ablation procedure, insight in the distribution of myocardium scar provides useful information for the physician. Specially, non-homogenous infarct regions (patchy infarcts (FIG. 6, 601) are known to trigger abnormal electric circuit in the ventricle wall. Moreover, post-procedural effect can be assessed by the described invention.

The embodiments described herein has been mainly disclosed with reference to MRI image datasets (in several forms). The skilled person would appreciate that this teaching can be equally extended to other imaging modalities, for instance computed tomography, Ultrasound, SPECT, PET, Ultrasound, rotational angiography, or the like. As example with focus on computed tomography (CT), the 3D roadmap model (FIG. 1, 105) can be created as well. Multiphase contrast enhanced CT would be equivalent with cine-MRI and allows calculated of mechanical activation (FIG. 1, 104), viability CT would be equivalent with delayed enhancement MRI and allow calculated of myocardium scar distribution (FIG. 1, 103). Coronary computed tomography angiography, allows assessment of coronary vein anatomy, as well as assessment of the phrenic nerve. Likewise, perfusion CT would be equivalent to perfusion MRI and allows incorporating myocardium ischemia into the 3D roadmap model.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited below or elsewhere herein are hereby incorporated by reference to the same extent as if each reference were individually and specifically indicated to be incorporated by reference and were set forth in its entirety herein.

The invention claimed is:

1. A method for providing guidance in Cardiac Resynchronization Therapy (CRT) comprising:
   a) receiving image data sets of the heart of a patient;
   b) creating a three-dimensional (3D) anatomical model of the cardiac structures from at least one of the image data sets;
   c) calculating myocardium infarct scar distribution using at least one of the image data sets;
   d) calculating heart mechanical activation data using at least one of the image data sets; and e) superimposing the scar distribution and the mechanical activation data on the 3D anatomical model to obtain a 3D roadmap model including anatomical geometry, mechanical activation data and scar distribution;

wherein the calculating of c) comprises:

segmenting a myocardium infarct scar to provide a 3D surface mesh of the scar or receiving data comprising myocardium infarct scar segmentation; and computing myocardium scar distribution by weighting infarct transmurality, endocardial transmurality, epicardial transmurality and infarct homogeneity, wherein the infarct transmurality is calculated as a percentage of a total infarct area inside a region covering an infarct, the endocardial transmurality is calculated as the infarct transmurality weighted with a distance value from an endocardial boundary, the epicardial transmurality is the infarct transmurality weighted with a distance value from an epicardial border, and the infarct homogeneity is calculated as an area of the detected infarct related to an area enclosed by a morphological close operator of a detected infarct.

2. The method according to claim 1, wherein the scar distribution is weighted with the mechanical activation data before superimposing to obtain a colour or grey value overlay on endocardial or epicardial 3D geometry.

3. The method according to claim 1, wherein the 3D anatomical model comprises information selected from the group consisting of: cardiac structures, infarct geometries, coronary vein geometry, phrenic nerve geometry or combination thereof.

4. The method according to claim 1, wherein the calculating of d) comprises calculating mechanical activation delay using myocardium 3D strain analysis.

5. The method according to claim 4, wherein mechanical activation delay is calculated by locating a time over a whole cardiac cycle corresponding to peak strain.

6. The method according to claim 1, wherein a segment or zone of the heart experiencing a latest mechanical activation is located and presented as outlined on the 3D anatomical model, the segment or zone experiencing the latest mechanical activation being a candidate segment or zone for optimal pacemaker lead positioning in the left ventricle in cardiac resynchronization therapy.

7. The method according to claim 1, wherein an infarct free segment or zone of the heart experiencing a latest mechanical activation is located and presented as outlined on the 3D anatomical model, the infarct free segment or zone experiencing the latest mechanical activation being a candidate segment or zone for optimal pacemaker lead positioning in cardiac resynchronization therapy.

8. The method according to claim 1, wherein the morphological close operator is configured to operate a division of the infarct area in chords and detect a non-infarct region between chords defining a patchy infarct region.

9. The method according to claim 1, wherein the 3D roadmap model identifies regions located on coronary veins having the latest electrical activation which is free from myocardium scar as optimal left ventricle lead position or positions.

10. The method according to claim 1, further comprising:
receiving an electro-anatomic mapping (EAM) model including 3D coronary vein anatomy and electrical activation timing; and registering the 3D roadmap model with the EAM model to determine optimal left ventricle lead position or positions.

11. The method according to claim 1, further comprising:
receiving patient specific x-ray image data; and
registering the 3D roadmap model with the x-ray image data to outline optimal left ventricle lead position or positions.

12. The method according to claim 1, wherein the calculating in d) includes:
i) segmenting LV myocardium within a short-axis cine-MRI image sequence and a long-axis cine-MRI image sequence;
ii) computing 3D strain by calculating 3D displacement field of the deformation of myocardium as segmented in i); and
iii) generating a 3D model of the LV endocardium or LV epicardium of the heart based on the 3D strain computed in ii).

13. The method according to claim 12, wherein in the generating of iii), the mechanical activation of the heart is color-coded on the surface of the 3D model by weighting mechanical activation with myocardium scar distribution.

14. The method according to claim 1, wherein the calculating in d) includes generating a 3D model of mechanical activation of the heart based on the image data sets, and wherein the 3D model of mechanical activation of the heart is combined with the 3D anatomical model to obtain the 3D roadmap model which is used to guide a user in placement of a pacemaker lead during a CRT implantation procedure.

15. The method according to claim 1, wherein the myocardium scar distribution is weighted with the mechanical activation data before superimposing as a colour or grey value overlay on the 3D anatomical model.

16. The method according to claim 1, further comprising:
receiving an x-ray image data set comprised of multiple image frames over time; and
registering the 3D roadmap model with the x-ray image data set for use in guiding a user in placement of a pacemaker lead during a CRT implantation procedure.

17. A non-transitory computer readable medium, having stored thereon, instructions, which when executed by a computing device, cause the computing device to perform a method for providing guidance in Cardiac Resynchronization Therapy (CRT) comprising:
a) receiving image data sets of the heart of a patient;
b) creating a three-dimensional (3D) anatomical model of the cardiac structures from at least one of the image data sets;
c) calculating myocardium infarct scar distribution using at least one of the image data sets;
d) calculating heart mechanical activation data using at least one of the image data sets; and
e) superimposing the scar distribution and the mechanical activation data on the 3D anatomical model to obtain a 3D roadmap model including anatomical geometry, mechanical activation data and scar distribution;

wherein the calculating of c) comprises:

segmenting a myocardium infarct scar to provide a 3D surface mesh of the scar or receiving data comprising myocardium infarct scar segmentation; and computing myocardium scar distribution by weighting infarct transmurality, endocardial transmurality, epicardial transmurality and infarct homogeneity, wherein the infarct transmurality is calculated as a percentage of a total infarct area inside a region covering an infarct, the endocardial transmurality is calculated as the infarct transmurality weighted with a distance value from an endocardial boundary, the epicardial transmurality is the infarct transmurality weighted with a distance value from an epicardial border, and the infarct homogeneity is calculated as an area of the detected infarct related to an area enclosed by a morphological close operator of a detected infarct.

18. An apparatus for acquiring an image data set of the heart of a patient, the apparatus comprising a data processing module configured to perform a method to determine a 3D roadmap for guidance in cardiac resynchronization therapy (CRT) comprising:
   a) receiving image data sets of the heart of a patient;
   b) creating a three-dimensional (3D) anatomical model of the cardiac structures from at least one of the image data sets;
   c) calculating myocardium infarct scar distribution using at least one of the image data sets;
   d) calculating heart mechanical activation data using at least one of the image data sets; and
   e) superimposing the scar distribution and the mechanical activation data on the 3D anatomical model to obtain a 3D roadmap model including anatomical geometry, mechanical activation data and scar distribution;
wherein the calculating of c) comprises:
   segmenting a myocardium infarct scar to provide a 3D surface mesh of the scar or receiving data comprising myocardium infarct scar segmentation; and
   computing myocardium scar distribution by weighting infarct transmurality, endocardial transmurality, epicardial transmurality and infarct homogeneity,
   wherein the infarct transmurality is calculated as a percentage of a total infarct area inside a region covering an infarct,
   the endocardial transmurality is calculated as the infarct transmurality weighted with a distance value from an endocardial boundary,
   the epicardial transmurality is the infarct transmurality weighted with a distance value from an epicardial border, and
   the infarct homogeneity is calculated as an area of the detected infarct related to an area enclosed by a morphological close operator of a detected infarct.

19. The apparatus according to claim 18, wherein the apparatus is an MRI apparatus configured to acquire cine-MRI datasets, delayed enhanced datasets, or coronary MRA datasets.

20. The apparatus according to claim 19, further comprising an x-ray apparatus configured to acquire x-ray venograms with or without contrast agents, wherein the data processing module is configured to calculate the 3D roadmap model for assisting placement of pacemaker leads.

* * * * *